US012496161B2

(12) United States Patent
Torrie et al.

(10) Patent No.: US 12,496,161 B2
(45) Date of Patent: Dec. 16, 2025

(54) MARKER FOR TRACKING OBJECTS IN MEDICAL PROCEDURES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Paul Alexander Torrie, Marblehead, MA (US); Philip A. Cormier, Newburyport, MA (US); Rafal Z Jezierski, Candia, NM (US); Nathan Zamarripa, Kittery Point, ME (US); Luis Carlos Fial Teixeira Ribeiro, Coimbra (PT); Rui Jorge Melo Teixeira, Tondela (PT)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 153 days.

(21) Appl. No.: 18/686,081

(22) PCT Filed: Oct. 17, 2022

(86) PCT No.: PCT/US2022/046857
§ 371 (c)(1),
(2) Date: Feb. 23, 2024

(87) PCT Pub. No.: WO2023/069347
PCT Pub. Date: Apr. 27, 2023

(65) Prior Publication Data

US 2025/0186162 A1 Jun. 12, 2025

Related U.S. Application Data

(60) Provisional application No. 63/257,196, filed on Oct. 19, 2021.

(51) Int. Cl.
*A61B 90/00* (2016.01)

(52) U.S. Cl.
CPC ...... *A61B 90/39* (2016.02); *A61B 2090/3916* (2016.02); *A61B 2090/3983* (2016.02);
(Continued)

(58) Field of Classification Search
CPC ............ A61B 90/39; A61B 2090/3916; A61B 2090/3983; A61B 2090/3987; A61B 2090/3991
See application file for complete search history.

(56) References Cited

U.S. PATENT DOCUMENTS

| | | | |
|---|---|---|---|
| 6,499,488 B1 | 12/2002 | Hunter et al. | |
| 7,007,699 B2 | 3/2006 | Martinelli et al. | |

(Continued)

FOREIGN PATENT DOCUMENTS

| | | | | |
|---|---|---|---|---|
| CN | 112998856 A * | 6/2021 | ............. | A61B 34/20 |
| WO | 2004075768 A2 | 9/2004 | | |

OTHER PUBLICATIONS

International Search Report and Written Opinion mailed Mar. 23, 2023 for International Application No. PCT/US2022/046857, 22 pages.

*Primary Examiner* — Chao Sheng
(74) *Attorney, Agent, or Firm* — Dickinson Wright PLLC

(57) ABSTRACT

Tracking objects in medical procedures. At least one example is a method comprising: retaining a bone marker on a distal end of an installation tool, the bone marker comprising a polyhedron having a fiducial pattern on each of at least three outward facing surfaces of the polyhedron, an externally-threaded screw extending distally from the polyhedron, and a flange proximate to an intersection of the polyhedron and the externally-threaded screw; positioning a distal end of the externally-threaded screw against a bone at
(Continued)

a marker location; screwing the externally-threaded screw into the bone by way of the installation tool; and trapping tissue against the bone beneath the flange.

25 Claims, 14 Drawing Sheets

(52) U.S. Cl.
CPC ................ *A61B 2090/3987* (2016.02); *A61B 2090/3991* (2016.02)

(56) References Cited

U.S. PATENT DOCUMENTS

| | | | |
|---|---|---|---|
| 9,877,795 | B2 | 1/2018 | Hao et al. |
| 10,433,911 | B2 | 10/2019 | Wang et al. |
| 10,499,996 | B2 | 12/2019 | De Almeida Barreto |
| 11,864,840 | B2 | 1/2024 | Cazal |
| 2014/0343405 | A1 | 11/2014 | Daon et al. |
| 2019/0076112 | A1 | 3/2019 | Montgomery, Jr. |
| 2020/0000527 | A1 * | 1/2020 | Cazal .................. A61B 90/361 |
| 2022/0354580 | A1 | 11/2022 | Liu et al. |
| 2022/0375114 | A1 | 11/2022 | Hunter et al. |

* cited by examiner

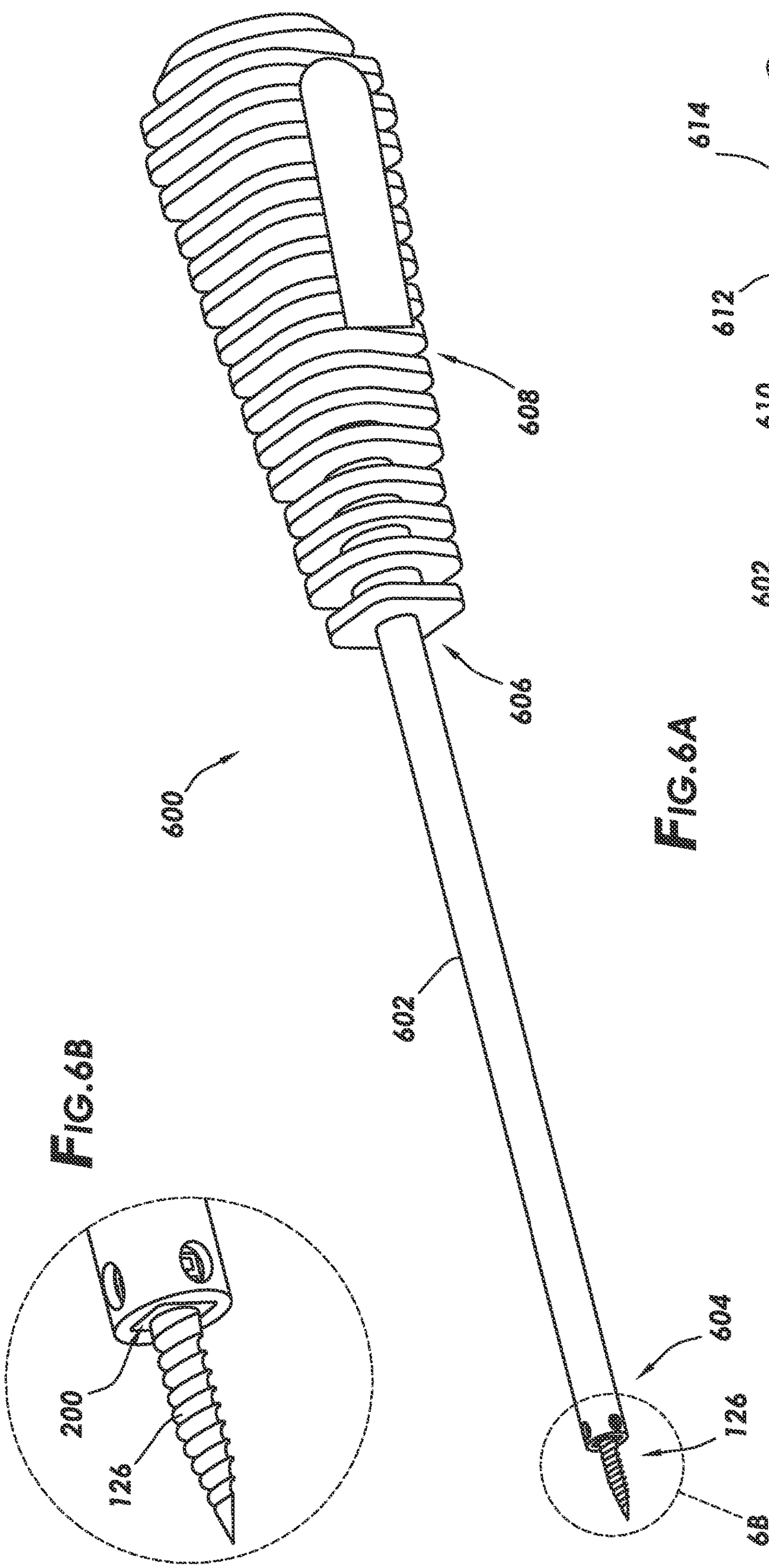
FIG. 6A
FIG. 6B
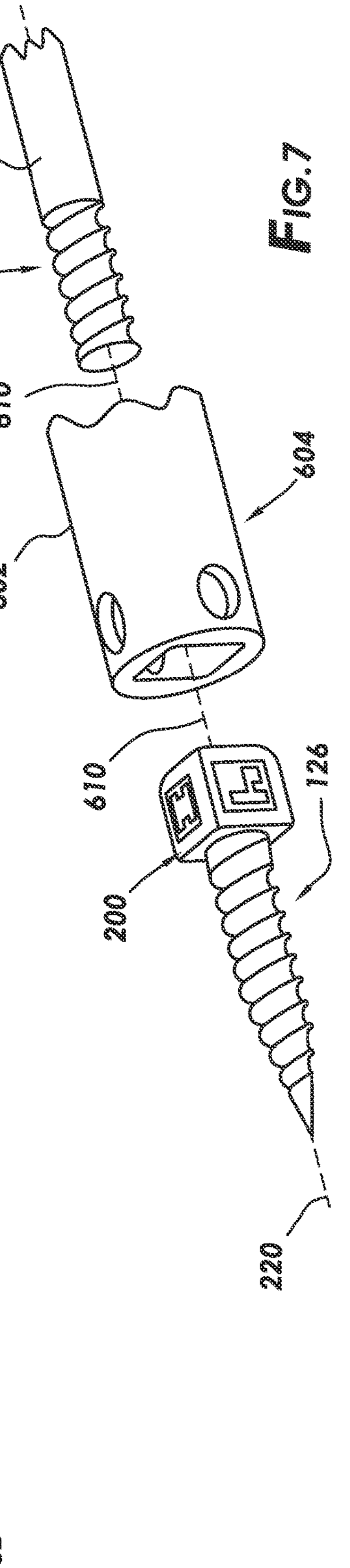
FIG. 7

MARKER FOR TRACKING OBJECTS IN MEDICAL PROCEDURES

CROSS-REFERENCE TO RELATED APPLICATIONS

This application a U.S. National Phase Entry of PCT App. No. PCT/US2022/046857 filed Oct. 17, 2022 and filled "Marker for Tracking Objects in Medical Procedures." The PCT application claims the benefit of U.S. provisional application Ser. No. 63/257,196 filed Oct. 19, 2021 titled "Methods and Systems of Tracking Objects in Medical Procedures." Both Applications are incorporated by reference herein as if reproduced in full below.

BACKGROUND

Arthroscopic surgical procedures are minimally invasive surgical procedures in which access to the surgical site within the body is by way of small keyholes or ports through the patient's skin. The various tissues within the surgical site are visualized by way of an arthroscope placed through a port, and the internal scene is shown on an external display device. The tissue may be repaired or replaced through the same or additional ports.

In computer-assisted surgical procedures (e.g., replacement of the anterior cruciate ligament (ACL), reduction of femora-acetabular impingement), the location of various objects with the surgical site may be tracked by way of images captured by the arthroscope. In particular, related-art systems teach tracking location of objects (e.g., medical instruments, bone) based on reading a quick response code (QR code), determining the orientation of the QR code within the three-dimensional coordinate space, and then determining the location and/or orientation of the attached instrument or bone within the three-dimensional coordinate space.

However, surgical sites may be filled with debris, loose tissue, and other objects that obscure QR code attached to a device. When the QR code is obscured, the computer-assistance is obviated.

SUMMARY

One example is a method comprising: retaining a bone marker on a distal end of an installation tool, the bone marker comprising a polyhedron having a fiducial pattern on each of at least three outward facing surfaces of the polyhedron, an externally-threaded screw extending distally from the polyhedron, and a flange proximate to an intersection of the polyhedron and the externally-threaded screw; positioning a distal end of the externally-threaded screw against a bone at a marker location; screwing the externally-threaded screw into the bone by way of the installation tool; and trapping tissue against the bone beneath the flange.

In the example method, retaining the bone marker may further comprise: telescoping the polyhedron into an internal volume at the distal end of the installation tool, the bone marker comprising a retention bore having an entrance aperture through an upper face of the polyhedron; and placing a retention fastener within the retention bore, the retention fastener retains the bone marker in a mating relationship with the installation tool. The example method may further comprise, after screwing the externally-threaded screw into the bone, removing the retention fastener from within the retention bore. In the example method, placing the retention fastener within the retention bore may further comprise threading external threads of the retention fastener into mating relationship with internal threads of the retention bore. The example method may further comprise, after screwing the externally-threaded screw into the bone, unscrewing the external threads of the retention fastener from the internal threads of the retention bore. Screwing the externally-threaded screw into the bone may further comprise applying force to the at least three outward facing surfaces of the polyhedron. Applying force to the at least three outward facing surfaces of the polyhedron may further comprise applying force at a location on each of the at least three outward facing surfaces that does not overlap the respective fiducial pattern on each of the at least three outward facing surfaces. Screwing the externally-threaded screw into the bone may further comprise applying force to the flange to the exclusion of the polyhedron.

In the example method, trapping tissue against the bone may further comprise trapping tissue between an exterior surface of the bone and a bottom face of the flange being a polymeric material.

In the example method, trapping tissue against the bone may further comprise trapping tissue between an exterior surface of the bone and a bottom face of the flange being a metallic material.

In the example method, trapping the tissue against the bone may further comprise trapping the tissue with the flange, and a vector normal to a plane defined by a portion of flange beneath the polyhedron forms an acute angle with a longitudinal central axis of the externally-threaded screw.

In the example method, trapping tissue against the bone may further comprise trapping tissue between an exterior surface of the bone and a bottom face of the flange defining at least one outside shape consisting of: circular; and oblong.

Yet another example is a bone marker comprising: a polyhedron defining a first outward-facing surface, a second outward-facing surface, and a third outward-facing surface; an externally-threaded screw projecting from a side of the polyhedron, the externally-threaded screw and polyhedron are monolithic; a retention bore having an entrance aperture through the polyhedron, the retention bore defining a retention feature on an inside surface of the retention bore; a first fiducial pattern on the first outward-facing surface, a second fiducial pattern on the second outward-facing surface, and a third fiducial pattern on the third outward-facing surface, the first, second, and third fiducial patterns distinct from each other; and a flange disposed proximate to an intersection of the polyhedron and the externally-threaded screw.

In the example bone marker, the polyhedron may be a cube. In the example bone marker, the externally-threaded screw may be a self-tapping screw.

In the example bone marker, the retention feature may further comprise threads defined on an inside surface of the retention bore. The example bone marker may further comprise externally-threaded screw being right-handed threads, and the threads on the inside surface of the retention bore being left-handed threads.

In the example bone marker the first, second, and third fiducial patterns may each be three dimensional patterns.

In the example bone marker, the flange may further comprise a polymeric material defining a top surface, a bottom surface opposite the top surface, a throughbore defining a throughbore axis, and a thickness measured parallel to throughbore axis, the throughbore telescoped over the externally-threaded screw, and the flange disposed at the intersection of a bottom face of the polyhedron and the proximal end of the externally-threaded screw. The flange may further comprise at least one material selected from a group consisting of: polymeric material; metallic material; and silicone. The flange may further comprise at least one shape selected from a group consisting of: circular; and oblong.

The example bone marker may further comprise: an annular trough disposed at the intersection of the polyhedron and a proximal end of the externally-threaded screw, the annular trough circumscribing a longitudinal central axis of the externally-threaded screw; and an inside diameter of the throughbore of the flange forming a friction fit with the annular trough.

The example bone marker may further comprise: an annular trough disposed at the intersection of the polyhedron and a proximal end of the externally-threaded screw, the annular trough circumscribing a longitudinal central axis of the externally-threaded screw; an installation thread defined between threads of the externally-threaded screw and the annular trough; and an inside diameter of the throughbore disposed within the annular trough.

In the example bone marker, the flange may further comprise: an upper surface that intersects the first, second, and third outward-facing surfaces; a lower surface that intersects the externally-threaded screw; a diameter greater than a largest dimension of the polyhedron measured perpendicular to a longitudinal central axis of the externally-threaded screw; and the flange, the polyhedron, and the externally-threaded screw are monolithic. The example bone marker may further comprise an interface feature defined by the flange, the interface feature being at least one selected from a group consisting of: an outside surface of the flange; an indention on the upper surface of the flange.

Another example is an intraoperative method comprising: receiving, by a surgical controller, images of a surgical site as viewed by an endoscope and attached camera head during a surgical procedure, the images including images of an instrument having a plurality of fiducials patterns associated with the instrument; selecting, by the surgical controller, a non-obscured fiducial pattern from the plurality of fiducial patterns that are visible in the images; calculating, by the surgical controller, a value indicative of location of the instrument within the surgical site based on the non-obscured fiducial pattern; and performing, by the surgical controller, an intraoperative task based on the value indicative of location.

In the example intraoperative method, receiving the images may further comprise receiving the images of the instrument being at least one selected from a group consisting of: a touch probe; and an aimer.

In the example intraoperative method, performing the intraoperative task may further comprise at least one selected from a group consisting of: register a location on a bone visible within the images; select a location for a revised-tunnel entry for a tunnel through a bone; select a location for a revised-tunnel exit for a tunnel through a bone; determine a location of a distal end of an aimer relative to a bone visible in the images; and determine an orientation of a longitudinal central axis of an aimer relative to an a central axis of a planned tunnel through the bone.

In the example intraoperative method, selecting a non-obscured fiducial pattern may further comprise selecting the non-obscured fiducial pattern whose normal vector is closest to coaxial with a view direction of an arthroscope.

In the example intraoperative method, receiving the images may further comprise receiving the images of the instrument having at least three fiducial surfaces, each of the at least three fiducial surfaces parallel to a longitudinal central axis of the instrument, and each of the at least three fiducial surfaces having a fiducial pattern thereon.

In the example intraoperative method, receiving the images may further comprise receiving the images of the instrument having a first fiducial surface having a first fiducial pattern thereon, a second fiducial surface having a second fiducial pattern thereon, and a third fiducial surface having a third fiducial pattern thereon, the first, second, and third fiducial surfaces at least partially forming an exterior surface around a longitudinal central axis of the instrument. Receiving the images may further comprise receiving the images having a fourth fiducial surface having a fourth fiducial pattern thereon, the first, second, third, and fourth fiducial surfaces forming an exterior surface around a longitudinal central axis of the instrument. Receiving the images further comprises receiving the images of the instrument wherein the first, second, and third fiducial surfaces are each parallel to the longitudinal central axis of the instrument.

In the example intraoperative method, receiving the images may further comprise receiving the images of the instrument having a first fiducial surface having a plurality of fiducial patterns thereon at distinct axial positions relative to a longitudinal central axis of the instrument, a second fiducial surface having a plurality of fiducial patterns thereon at distinct axial positions relative to the longitudinal central axis, a third fiducial surface having a plurality of fiducial patterns thereon at distinct axial positions relative to the longitudinal central axis. Receiving the images may further comprise receiving the images of the instrument having a fourth fiducial surface having a plurality of fiducial patterns thereon at distinct axial positions relative to the longitudinal central axis. In the example intraoperative method, each of the plurality of fiducial patterns on the first fiducial surface may be identical. In the example intraoperative method, each of the plurality of fiducial patterns on the first fiducial surface may be distinct.

Yet another example is a medical instrument comprising: an elongate shaft defining a proximal end, a distal end, and a longitudinal central axis; a first fiducial surface disposed proximate to the distal end, and a first fiducial pattern disposed on the first fiducial surface; a second fiducial surface disposed proximate to the distal end, and a second fiducial pattern disposed on the second fiducial surface; a third fiducial surface disposed proximate to the distal end, and a third fiducial pattern disposed on the third fiducial surface; and the first, second, and third fiducial surfaces at least partially forming an exterior surface around the longitudinal central axis.

The example medical instrument may further comprise the elongate shaft defining a throughbore from the proximal end to the distal end. The example medical instrument may further comprise: a fourth fiducial surface disposed proximate to the distal end, and a fourth fiducial pattern disposed on the fourth fiducial surface; and the first, second, third, and fourth fiducial surfaces define the exterior surface around the longitudinal central axis. The example medical instrument may further comprise: the first fiducial surface defines a plane perpendicular to the second fiducial surface; the second fiducial surface defines a plane perpendicular to the third fiducial surface; the third fiducial surface defines a plane perpendicular to the fourth fiducial surface; and the fourth fiducial surface defines a plane perpendicular to the first fiducial surface. The first, second, third, and fourth fiducial patterns may be identical.

The example medical instrument may further comprise a probe end that defines a probe axis, the probe axis forms an acute angle with the longitudinal central axis, the acute angle measured beyond the distal end of the medical instrument. The example medical instrument may further comprise: the first fiducial surface defines a plane that intersects a plane defined by the second fiducial surface; the plane defined by the second fiducial surface intersects a plane defined by the third fiducial surface; the plane defined by the third fiducial surface intersects the plane defined by the first fiducial surface; and a cross-sectional shape, taken perpendicular the longitudinal central axis, is triangular. The geometric center of the cross-sectional shape may have a non-zero offset from the longitudinal central axis.

The example medical instrument may further comprise: the first fiducial surface comprises a first plurality of fiducial patterns of which the first fiducial pattern is a member, each fiducial pattern of the first plurality of fiducial patterns at a distinct axial position relative to the longitudinal central axis; the second fiducial surface comprises a second plurality of fiducial patterns of which the second fiducial pattern is a member, each fiducial pattern of the second plurality of fiducial patterns at a distinct axial position relative to the longitudinal central axis; and the third fiducial surface comprises a third plurality of fiducial patterns of which the third fiducial pattern is a member, each fiducial pattern of the third plurality of fiducial patterns at a distinct axial position relative to the longitudinal central axis. Each of the first, second, and third plurality of fiducial patterns may be identical. Each of the first plurality of fiducial patterns may be distinct from each other and distinct from each of the second, and third fiducial patterns.

Another example is a surgical controller comprising: a processor configured to couple to a display device; and a memory coupled to the processor. The memory may store instructions that, when executed by the processor, cause the processor to: receive images of a surgical site as viewed by an endoscope and attached camera head during a surgical procedure, the images including images of an instrument having a plurality of fiducials patterns associated with the instrument; select a non-obscured fiducial pattern from the plurality of fiducial patterns that are visible in the images; calculate a value indicative of location of the instrument within the surgical site based on the non-obscured fiducial pattern; and perform an intraoperative task based on the value indicative of location.

In the example surgical controller, when the processor receives the images, the instructions may further cause the processor to receive the images of the instrument being at least one selected from a group consisting of: a touch probe; and an aimer.

In the example surgical controller, when the processor performs the intraoperative task, the instructions nay further cause the processor to at least one selected from a group consisting of: register a location on a bone visible within the images; select a location for a revised-tunnel entry for a tunnel through a bone; select a location for a revised-tunnel exit for a tunnel through a bone; determine a location of a distal end of an aimer relative to a bone visible in the images; and determine an orientation of a longitudinal central axis of an aimer relative to a central axis of a planned tunnel through the bone.

In the example surgical controller, when the processor selects a non-obscured fiducial pattern, the instructions may further cause the processor to select the non-obscured fiducial pattern whose normal vector is closest to coaxial with a view direction of an arthroscope.

In the example surgical controller, when the processor receives the images, the instructions may further cause the processor to receive the images of the instrument having at least three fiducial surfaces, each of the at least three fiducial surfaces parallel to a longitudinal central axis of the instrument, and each of the at least three fiducial surfaces having a fiducial pattern thereon.

In the example surgical controller, when the processor receives the images, the instructions may further cause the processor to receive the images of the instrument having a first fiducial surface having a first fiducial pattern thereon, a second fiducial surface having a second fiducial pattern thereon, and a third fiducial surface having a third fiducial pattern thereon, the first, second, and third fiducial surfaces at least partially define an exterior surface around a longitudinal central axis of the instrument. When the processor receives the images, the instructions may further cause the processor to receive the images having a fourth fiducial surface having a fourth fiducial pattern thereon, the first, second, third, and fourth fiducial surfaces form an exterior surface around a longitudinal central axis of the instrument.

In the example surgical controller, when the processor receives the images, the instructions may further cause the processor to receive the images of the instrument wherein the first, second, and third fiducial surfaces are each parallel to the longitudinal central axis of the instrument.

In the example surgical controller, when the processor receives the images, the instructions may further cause the processor to receive the images of the instrument having a first fiducial surface having a plurality of fiducial patterns thereon at distinct axial positions relative to a longitudinal central axis of the instrument, a second fiducial surface having a plurality of fiducial patterns thereon at distinct axial positions relative to the longitudinal central axis, a third fiducial surface having a plurality of fiducial patterns thereon at distinct axial positions relative to the longitudinal central axis. When the processor receives the images, the instructions may further cause the processor to receive the images of the instrument having a fourth fiducial surface having a plurality of fiducial patterns thereon at distinct axial positions relative to the longitudinal central axis. Each of the plurality of fiducial patterns on the first fiducial surface may be identical. Each of the plurality of fiducial patterns on the first fiducial surface may be distinct.

BRIEF DESCRIPTION OF THE DRAWINGS

For a detailed description of example embodiments, reference will now be made to the accompanying drawings in which:

FIGS. 6A and 6B show a perspective view of a bone marker retained on a distal end of an installation tool in accordance with at least some embodiments;

FIG. 7 shows an exploded perspective view of the distal end of the installation tool and the bone marker, in accordance with at least some embodiments;

DEFINITIONS

Figure 1:
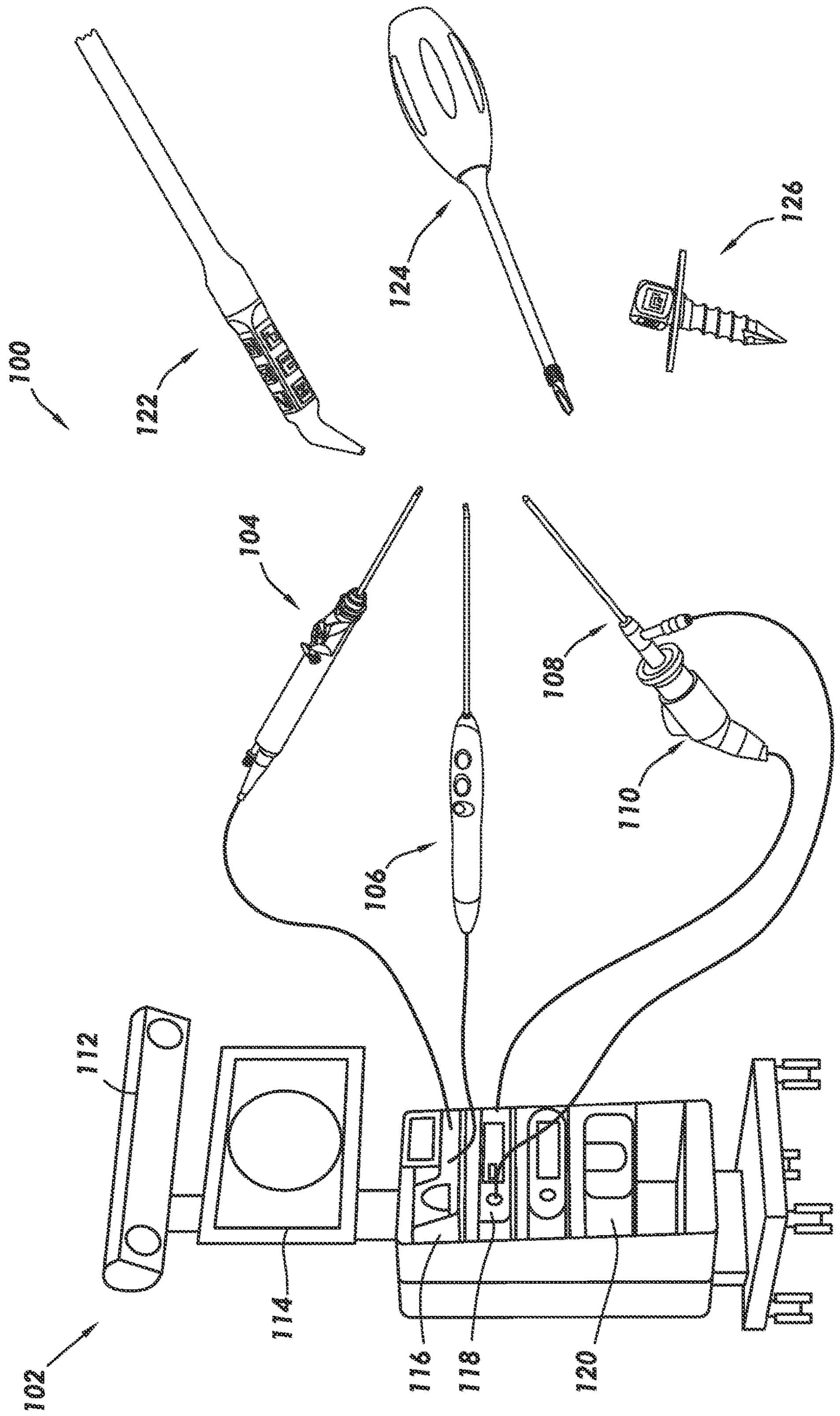
FIG. 1 shows a surgical system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"Throughbore" shall mean an aperture or passageway through an underlying object. However, the term "throughbore" shall not be read to imply any method of creation. Thus, a throughbore may be created in any suitable way, such as drilling, boring, laser drilling, or casting.

"Counterbore" shall mean an aperture or passageway into an underlying object. In cases in which the counterbore intersects another aperture (e.g., a throughbore), the counter bore may thus define an internal shoulder. However, the term "counterbore" shall not be read to imply any method of creation. A counterbore may be created in any suitable way, such as drilling, boring, laser drilling, or casting.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to methods and systems of tracking objects in medical procedures. More particularly, various examples are directed to methods and related systems to reduce occurrence of debris and/or tissue obscuring fiducial patterns attached to objects (e.g., bone marker, medical instruments) in arthroscopic surgical procedures. More particularly still, example methods and systems duplicate fiducial patterns at varying positions around and/or along a tracked object such that, to the extent debris and/or tissue obscures one fiducial pattern, another fiducial pattern may nevertheless be visible, and thus the computer assistance may still be available. In the example case of a bone marker, the bone marker may comprise a polyhedron with fiducial patterns on several outward-facing surfaces. Additionally, the bone marker may comprise a flange to compress or trap underlying tissue to reduce occurrences of the underlying tissue obscuring the fiducial patterns. In the example case of a medical instrument disposed within the surgical site, the medical instrument may comprise a plurality of fiducial patterns disposed around the medical instrument and/or a plurality of fiducial patterns disposed at differing axial positions along the medical instrument. Implementing the plurality of fiducial patterns reduces occurrence of the computer assistance losing track of location of the medical instrument within the surgical site based on debris and/or tissue obscuring the fiducial patterns. The specification first turns to an example system to orient the reader.

FIG. 1 shows a surgical system (not to scale) in accordance with at least some embodiments. In particular, the example surgical system 100 comprises a tower or device cart 102, an example mechanical resection instrument 104, an example plasma-based ablation instrument (hereafter just ablation instrument 106), and an endoscope in the example form of an arthroscope 108 and attached camera head 110. The device cart 102 may comprise a camera 112 (illustratively shown as a stereoscopic camera), a display device 114, a resection controller 116, and a camera control unit (CCU) together with an endoscopic light source and video controller. In example cases the CCU, endoscopic light source, and video controller not only provide light to the arthroscope 108 and display images received from the camera head 110, but also implement various additional aspects, such as tracking location of objects within the surgical site. Thus, the CCU, endoscopic light source, and video controller are hereafter referred to as a surgical controller 118. In other cases, however, the CCU, endoscopic light source, and video controller may be a separate and distinct systems from the controller that handles aspects of intraoperative tracking, yet the separate devices would nevertheless be operationally coupled.

The example device cart 102 further includes a pump controller 120 (e.g., single or dual peristaltic pump). Fluidic connections of the mechanical resection instrument 104 and ablation instrument 106 are not shown so as not to unduly complicate the figure. Similarly, fluidic connections between the pump controller 120 and the patient are not shown so as not to unduly complicate the figure. In the example system, both the mechanical resection instrument 104 and the ablation instrument 106 are coupled to the resection controller 116 being a dual-function controller. In other cases, however, there may be a mechanical resection controller separate and distinct from an ablation controller. The example devices and controllers associated with the device cart 102 are merely examples, and other examples include vacuum pumps, robotic arms holding various instruments, ultrasonic cutting devices and related controllers, patient-positioning controllers, and robotic surgical systems.

FIG. 1 further shows additional instruments that may be present during an arthroscopic surgical procedure. In particular, FIG. 1 shows an example touch probe 122, an aimer 124, and a bone marker 126. The touch probe 122 may be used during the surgical procedure to provide information to the surgical controller 118, such as: information to register a three-dimensional bone model to an underlying bone visible in images captured by the arthroscope 108 and camera head 110; and information as to a revised tunnel-entry location and/or a revised tunnel-exit location when the surgeon elects to deviate from the preoperative tunnel plan. The aimer 124 may be used as a guide for placement and drilling with a drill wire to create an initial or pilot tunnel through the bone. The bone marker 126 may be rigidly attached to the bone and serve as an anchor location for the surgical controller 118 to know the orientation of the bone (e.g., after registration of a three-dimensional bone model). Additional tools and instruments will be present, such as the drill wire, various reamers for creating the throughbore and counterbore aspects of a tunnel through the bone, and various tools, such as for suturing and anchoring a graft. These additional tools and instruments are not shown so as not to further complicate the figure.

Figure 2:
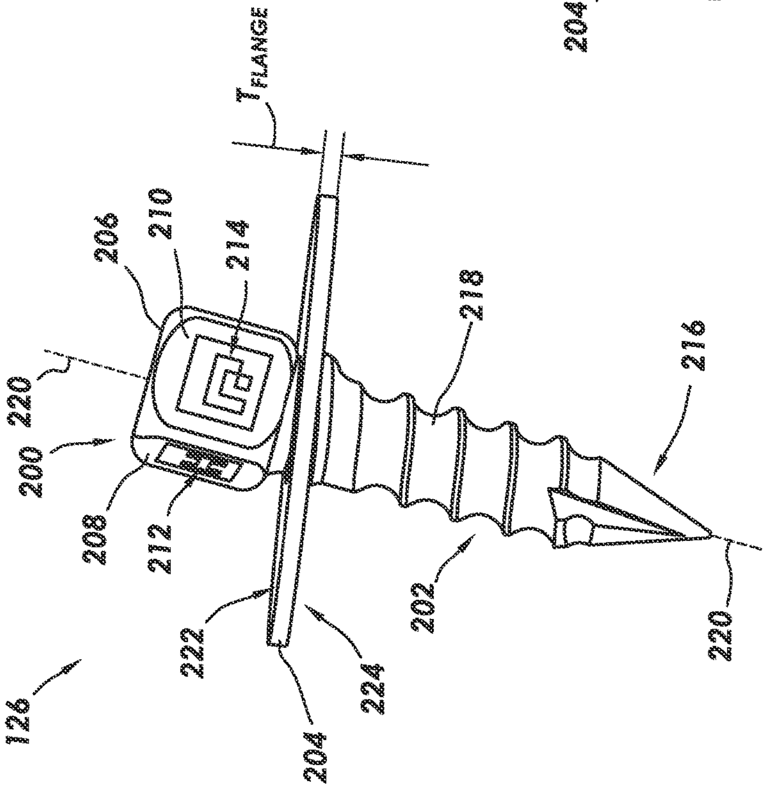
FIG. 2 shows a perspective side view of a bone marker in accordance with at least some embodiments.

FIG. 2 shows a perspective side view of an example bone marker 126. In particular, the example bone marker 126 comprises a polyhedron 200, an externally-threaded screw 202, and a flange 204. The example polyhedron defines an upper surface or upper face 206, and a plurality of outward-facing surfaces, such as outward-facing surface 208 and outward-facing surface 210. In the example of FIG. 2, the polyhedron 200 is a cube, and thus two additional outward-facing surfaces are present but are not visible in the view of FIG. 2. However, the polyhedron 200 may take any suitable shape which defines an upper face 206, at least three outward-facing surfaces, and a location (e.g., a lower face) from which the externally-threaded screw 202 protrudes. Each of the outward-facing surfaces, such as outward-facing surfaces 208 and 210 visible in FIG. 2, have disposed thereon a fiducial pattern, such as fiducial patterns 212 and 214, respectively. Referring to fiducial pattern 214 as representative, the fiducial pattern 214 is a machine readable code that uniquely identifies the outward-facing surface 210 of the polyhedron 200. That is, the surgical controller 118 (FIG. 1), receiving images captured by the arthroscope 108 (FIG. 1) and camera head 110 (FIG. 1), may read a value represented by the fiducial pattern 214. Moreover, the fiducial pattern 214 is designed and constructed such that, by analyzing physical relationships of the three-dimensional features or patterns of the fiducial pattern 214 (e.g., outside corners, inside corners, relative line widths) within the images of the fiducial pattern 214, the surgical controller 118 may thus determine the physical orientation of the fiducial pattern and thus the bone marker 126 in the three-dimensional coordinate space in the view of the arthroscope 108. It follows that, when the bone marker 126 is coupled to a bone, the surgical controller 118 may determine the physical orientation of the attached bone in the three-dimensional coordinate space in the view of the arthroscope 108. In example systems, the fiducial pattern on each of the outward-facing surfaces is a unique and distinct pattern.

In the example, the externally-threaded screw 202 projects from a side of the polyhedron 200 opposite from the upper face 206. In example cases, the polyhedron 200 and the externally-threaded screw 202 are a monolithic structure, such as a continuous piece of metallic material (e.g., aluminum). For example, the polyhedron 200 and the externally-threaded screw 202 may be simultaneously cast within a mold, or may be milled from single piece of aluminum, stainless steel, or titanium. The example externally-threaded screw 202 is a self-drilling or self-tapping screw, meaning that the distal end 216 of the externally-threaded screw 202 comprises a drilling feature to create the initial aperture into the bone. The externally-threaded screw 202 further comprises threads 218 extending from near the distal end 216 toward the proximal end of the externally-threaded screw 202. In some cases the threads 218 are right-handed threads, meaning the bone marker 126 is turned clockwise about its longitudinal central axis 220, viewed from above the polyhedron 200 looking along the longitudinal central axis toward the externally-threaded screw, when the bone marker 126 is being screwed into a bone. The threads 218 may alternatively be left-handed threads.

The bone marker 126 is a relatively small object—in one example the outside diameter of the externally-threaded screw 202 is about 2.5 millimeters (mm)—though larger and smaller sizes are contemplated. In example cases, the polyhedron 200 may form faces that are about 4 mm in length (measured parallel to the longitudinal central axis 220). In some cases, the fiducial patterns on each face are the same size, but in other cases the fiducial patterns (even for duplicate patterns) need not have the same size. The overall length of example bone markers may be from 10 mm to 15 mm, inclusive, and in one example 12 mm.

Still referring to FIG. 2, the example bone marker 126 further comprises the flange 204. The example flange 204 is disposed proximate to an intersection of the polyhedron 200 and the externally-threaded screw 202. The example flange 204 is a separate and distinct component from the monolithic structure of the polyhedron 200 and externally-threaded screw 202. The flange 204 may be made of a metallic material (e.g., aluminum); however, in other cases the flange 204 may be made of a polymeric material (e.g., silicone) to enable the flange 204 to conform to the shape of the underlying bone as the bone marker 126 is screwed into the bone. The flange 204 defines a top surface 222, a bottom surface 224 opposite the top surface 222, a throughbore (not visible in FIG. 2) defining a throughbore axis, a diameter (e.g., about 9 mm) and a thickness $T_{FLANGE}$ measured parallel to throughbore axis. In example cases, and as shown, the thickness $T_{FLANGE}$ of the flange 204 is uniform from the throughbore to the outer edge of the flange 204. However, in other cases a non-uniform thickness may be used, such as a tapered thickness having a greater thickness near the throughbore and thinner with increasing distance from the throughbore toward the outside edge.

Figure 3:
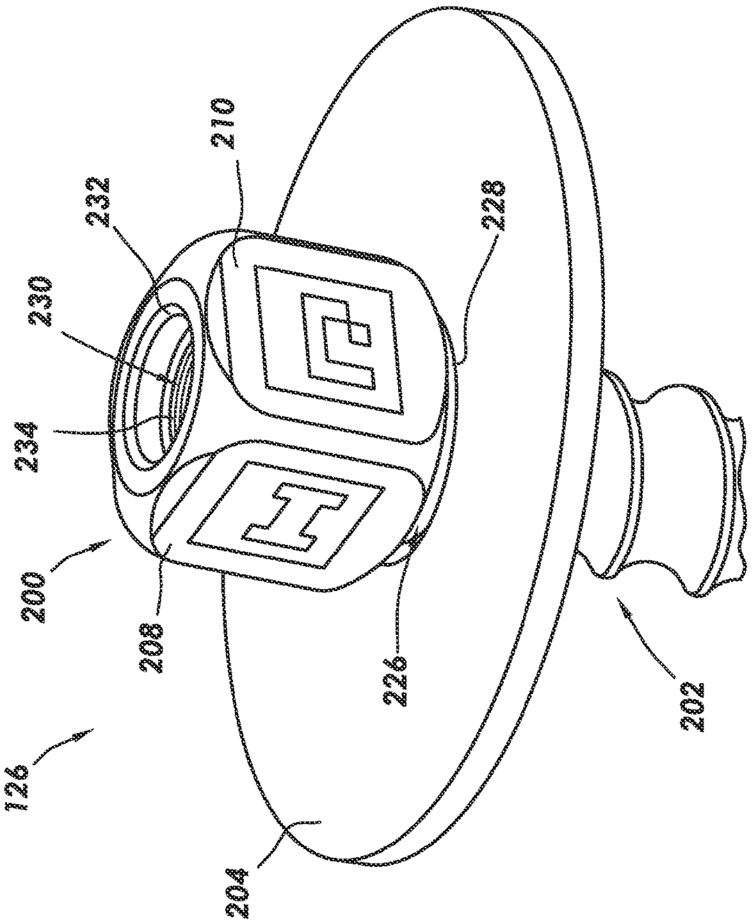
FIG. 3 shows a perspective side view of a bone marker in accordance with at least some embodiments.

FIG. 3 shows a perspective view of the example bone marker 126. In particular, visible in FIG. 3 is the polyhedron 200 and a portion of the externally-threaded screw 202. The outward-facing surfaces 208 and 210 are also visible, with their respective fiducial patterns (not specifically numbered). In the view of FIG. 3, however, the throughbore 226 through the flange 204 is visible, along with an annular trough 228 disposed at the intersection of the polyhedron 200 and a proximal end of the externally-threaded screw 202. After installation and/or creation, the inside diameter of the throughbore 226 is disposed within the annular trough 228. As shown in FIGS. 2 and 3, the example flange 204 may shift within the annular trough 228 so as to conform to the orientation of the underlying bone or soft tissue during installation of the bone marker 126.

Still referring to FIG. 3, the example bone marker 126 further comprises a retention bore 230 having an entrance aperture 232 through the upper face 206 of the polyhedron 200. The retention bore 230 defines a retention feature 234, illustratively shown as threads on an inside surface of the retention bore 230. The retention feature 234 may be used to retain the bone marker 126 in operational relationship with an installation tool (not shown in FIG. 3) such that the un-installed bone marker 126 may be placed through the port through the patient's skin, and then screwed in place into the bone. Once screwed in place, the installation tool may release from the retention feature 234, enabling the installation tool to be withdrawn and leaving the bone marker 126 in place. The flange 204 may be opaque, transparent, or anything in between.

Figure 4:
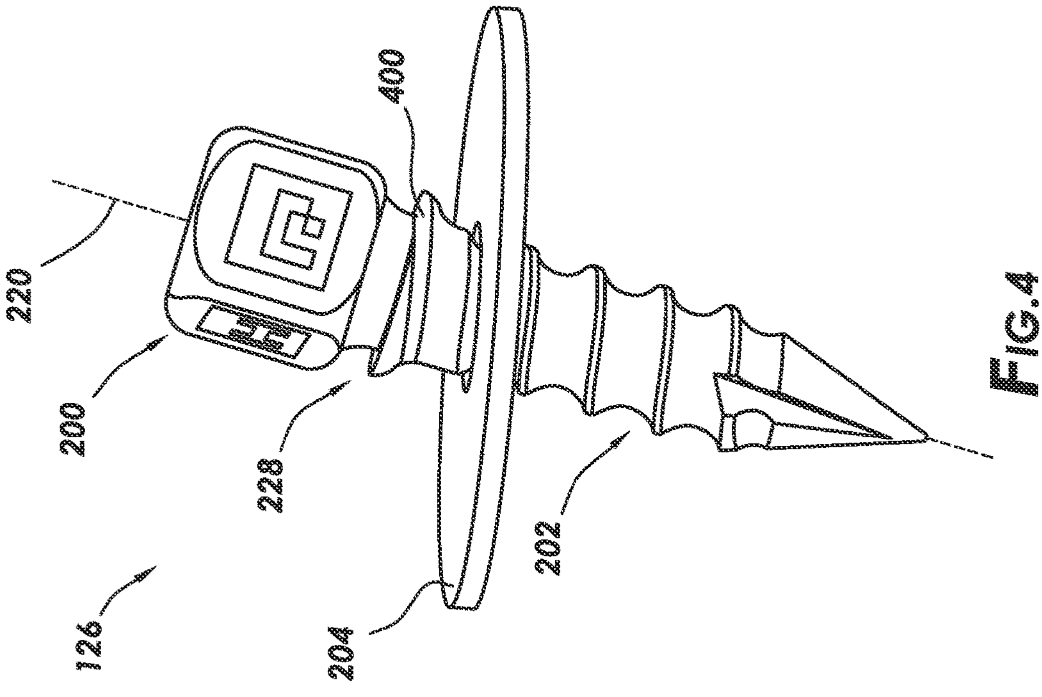
FIG. 4 shows a perspective side view of a bone marker in accordance with at least some embodiments.

FIG. 4 shows a perspective side view of the example bone marker 126 with the flange 204 displaced away from the polyhedron 200. In particular, better visible in FIG. 4 is the annular trough 228. The annular trough 228 is disposed between the polyhedron 200 and the proximal end of the externally-threaded screw 202, and the example annular trough 228 circumscribes the longitudinal central axis 220 of the bone marker 126. In example cases in which the flange 204 is a rigid material, the example bone marker 126 may comprises an installation thread 400, providing a channel from the outside the annular trough 228 to within the annular trough 228. The installation thread 400 enables the installation of the flange 204 such that the inside diameter of the throughbore 226 resides within the annular trough 228. In other cases, however, the installation thread 400 may be omitted. For example, when the flange 204 is made of a polymeric material, the flange 204 may be elastically deformed during installation to place the inside diameter of the flange 204 within the annular trough 228. In yet still other cases, the flange 204 may be cast in place with the annular trough 228 forming a portion of the mold used to cast the flange 204. Any suitable method or system may be used to install the flange 204 to the bone marker 126.

Figure 5:
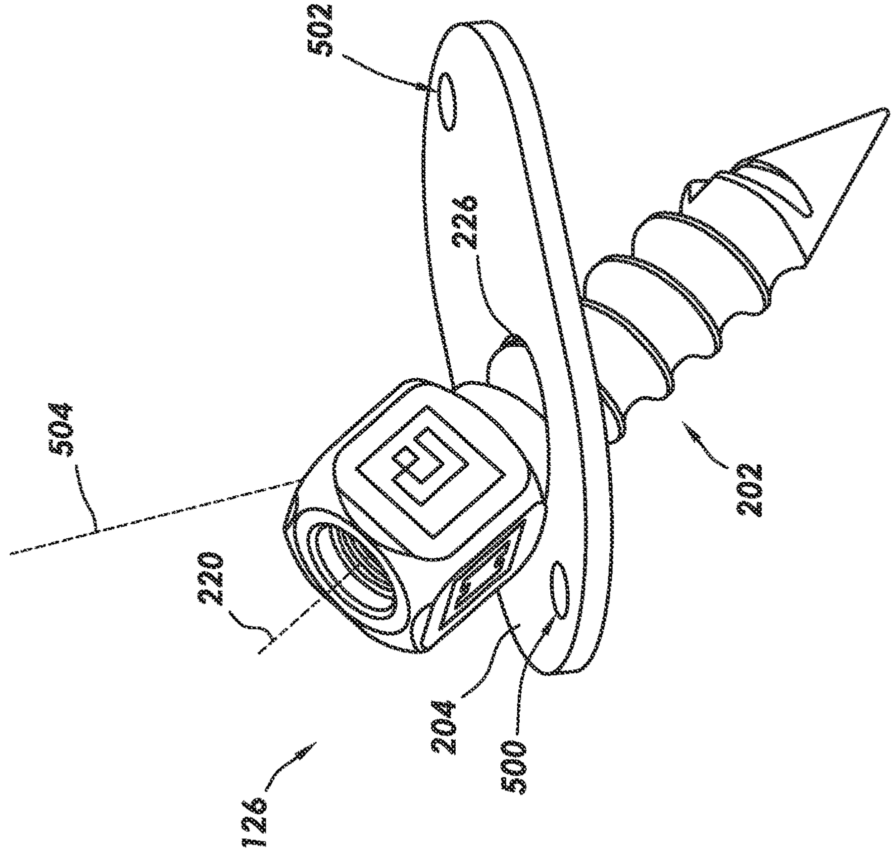
FIG. 5 shows a perspective view of a bone marker in accordance with at least some embodiments.

FIG. 5 shows a perspective view of another example bone marker 126 to show various alternatives. In particular, the example bone marker 126 of FIG. 5 includes the flange 204; however, the example flange 204 of FIG. 5 is shown to have an elliptical or oblong shape. That is, when viewed from above and along a throughbore axis, the outside edge or outside surface defines an oblong shape. The throughbore 226 is show off-center with the respect to the oblong shape (e.g., at the focus of the ellipse), but the throughbore may be placed in any suitable location. The example flange 204 of FIG. 5 further comprises throughbores 500 and 502 disposed on opposite ends of the long dimension of the flange 204. The throughbores 500 and/or 502 may be used to help position the flange 204 in an orientation desired by the surgeon prior to final tightening of the bone marker 126 into the bone. The example oblong-shaped flange 204 may find particular use in arthroscopic ACL repair in which the bone marker 126 is placed on the tibial plateau. In such locations, there may be tissue protruding from the plateau's surfaces, and the oblong shape may thus enable the flange to capture or trap tissue between the bone and lower surface of the flange 204 beneath the polyhedron 200. In one example, the largest dimension of the oblong shape of the example flange 204 of FIG. 5 is about 16 mm.

FIG. 5 further shows that in other examples the throughbore 226 need not be retained in an annular trough. As shown, the throughbore 226 is telescoped over the externally-threaded screw 202, but the relative orientations of the throughbore axis 504 of the throughbore 226 and the longitudinal central axis 220 of the polyhedron 200 may be greater for the example systems of FIG. 5. Further still, FIG. 5 shows that the throughbore 226 itself need not be circular. The inside surface of the example throughbore 226 of FIG. 5 may form an oblong shape, when viewed along the throughbore axis 504, to enable greater relative orientations between the central axis 504 and the longitudinal central axis 220.

The alternatives of FIG. 5 shall not be read as mutually exclusive. For example, an oblong-shaped flange may be designed and constructed to have the inside diameter of the throughbore 226 disposed within an annular trough 228 (FIG. 2). Oppositely, a circular-shaped flange may be designed and constructed to have the throughbore floating as shown in FIG. 5, including a throughbore that defines an oblong shape. Further, the oblong-shaped flange 204 shown in FIG. 5 may rotate about marker axis 220 or it may be rotationally keyed to the marker 202. The discussion now turns to retaining the example bone marker 126 in an installation tool during placement of the bone marker 126 into bone.

FIG. 6A shows a perspective view of the bone marker 126 retained on a distal end of an example installation tool. In particular, FIG. 6A shows an example installation tool 600 comprising an elongate shaft 602 defining a distal end 604 and a proximal end 606. The elongate shaft 602 is coupled on the proximal end 606 to a handle 608. Though not visible in FIG. 6A, the elongate shaft 602 and handle 608 define coaxial throughbores. Also visible in FIG. 6A is an example bone marker 126 with the flange omitted so as not to obscure the intersection of the bone marker 126 and the distal end 604 of the installation tool 600. FIG. 6B shows a magnified view of the distal end 604 comprising the bone marker 126. In the example, the bone marker 126 is retained within the installation tool 600 by the telescoping the polyhedron 200 into an internal volume at the distal end 604 of the installation tool 600. As will be shown and discussed in greater detail below, the bone marker 126 is retained in the telescoped relationship by way of a retention fastener (not visible in FIG. 6A or 6B) placed in mating relationship with a retention feature 234 (FIG. 2) within the retention bore 230 (FIG. 2). The retention fastener provides an axial force tending to hold the bone marker 126 in the telescoped relationship. Retaining the bone marker 126 within the installation tool enables installation of the bone marker 126 directly, and eliminates the related-art approach of drilling a pilot tunnel with a guide wire and then sliding the bone marker along the guide to direct the bone marker to the correct location on the bone.

During use, the distal end 604 of the installation tool 600 and the retained bone marker 126 are placed within the surgical site, such as through a port through the patient's skin. The installation tool 600 may then be used to not only place the bone marker 126 in a suitable location for installation (e.g., in the intercondylar notch for an ACL repair/replacement), but also to provide rotational force to the bone marker 126 to enable the externally-threaded screw to enter the bone and affix the bone marker 126 to the bone. In order to reduce the chances of denting or damaging the fiducial patterns on the outward-facing surfaces of the polyhedron 200, in example cases the rotational force applied to the polyhedron 200 by the installation tool 600 is at a location on each of the outward-facing surfaces that does not touch or overlap the respective fiducial pattern on the outward-facing surfaces. Stated otherwise, the rotational force for installation of the bone marker 126 is applied on each outward-facing surface at a location outside the boundaries of the respective fiducial pattern.

FIG. 7 shows an exploded perspective view of the distal end of the installation tool 600 and the bone marker 126. In particular, the distal end 604 of the elongate shaft 602 defines an inside surface designed and constructed to telescope over the polyhedron 200 of the bone marker 126. In the example case of the polyhedron 200 being a cube, the inside surface of the distal end 604 of the elongate shaft thus defines a square cross-sectional shape. The elongate shaft 602 further defines a throughbore along the longitudinal central axis 610 of the elongate shaft 602. The throughbore intersects the inside surface creating a shoulder region (not specifically shown) that limits axial translation of the polyhedron 200 into the distal end 604. Telescoped within the throughbore and along the longitudinal central axis 610 is a retention fastener 612 illustratively shown as an externally threaded portion of an elongate rod 614. The elongate rod 614 may extend to and through handle 608 (FIG. 6A) to the distal end 604.

Retaining the bone marker 126 on the distal end 604 of the installation tool 600 may thus comprise telescoping the polyhedron 200 into the internal volume defined by the inside surface at the distal end 604 of the installation tool 600. The retention fastener 612 may then be coupled to retention feature 234 (FIG. 2) within the retention bore 230 (FIG. 2) on the upper face of the polyhedron 200. In the example shown, the retention fastener 612 in the form of external threads may threadingly couple to the retention feature 234 in the form of internal threads within the retention bore 230. The elongate rod 614 may thus provide a force tending to hold the bone marker 126 in mating relationship with the installation tool 600. In the example, when the bone marker 126 is retained in mating relationship with the installation tool, the longitudinal central axis 220 of the bone marker 126 is coaxial with the longitudinal central axis 610 of the throughbore of the elongate shaft 602 and the longitudinal central axis of the elongate rod 614. In other cases, however, the longitudinal central axes need not be coaxial.

Once the bone marker 126 is placed in the bone, the retention fastener 612 may be detached from the retention bore 230 (FIG. 2). In particular, in the example case of the retention fastener 612 being external threads, the installation tool 600 may be used to hold the bone marker 126 in a constant rotational orientation while the external threads of the retention fastener 612 are unscrewed from mating relationship. In some cases, the threads of the example retention fastener 612 are right-handed threads, but the given that the bone marker 126 may be held in place with the installation tool 600, unscrewing the threads of the example retention fastener 612 does not unscrew the bone marker 126 from the bone. In other cases, however, the threads of the example retention fastener 612 may be left-handed threads and the threads of the externally-threaded screw 202 may be right-handed threads (or vice versa), such that the act of unscrewing the threads of the example retention fastener 612 will tend to further tighten the connection of the bone marker 126 to the underlying bone.

Figure 18:
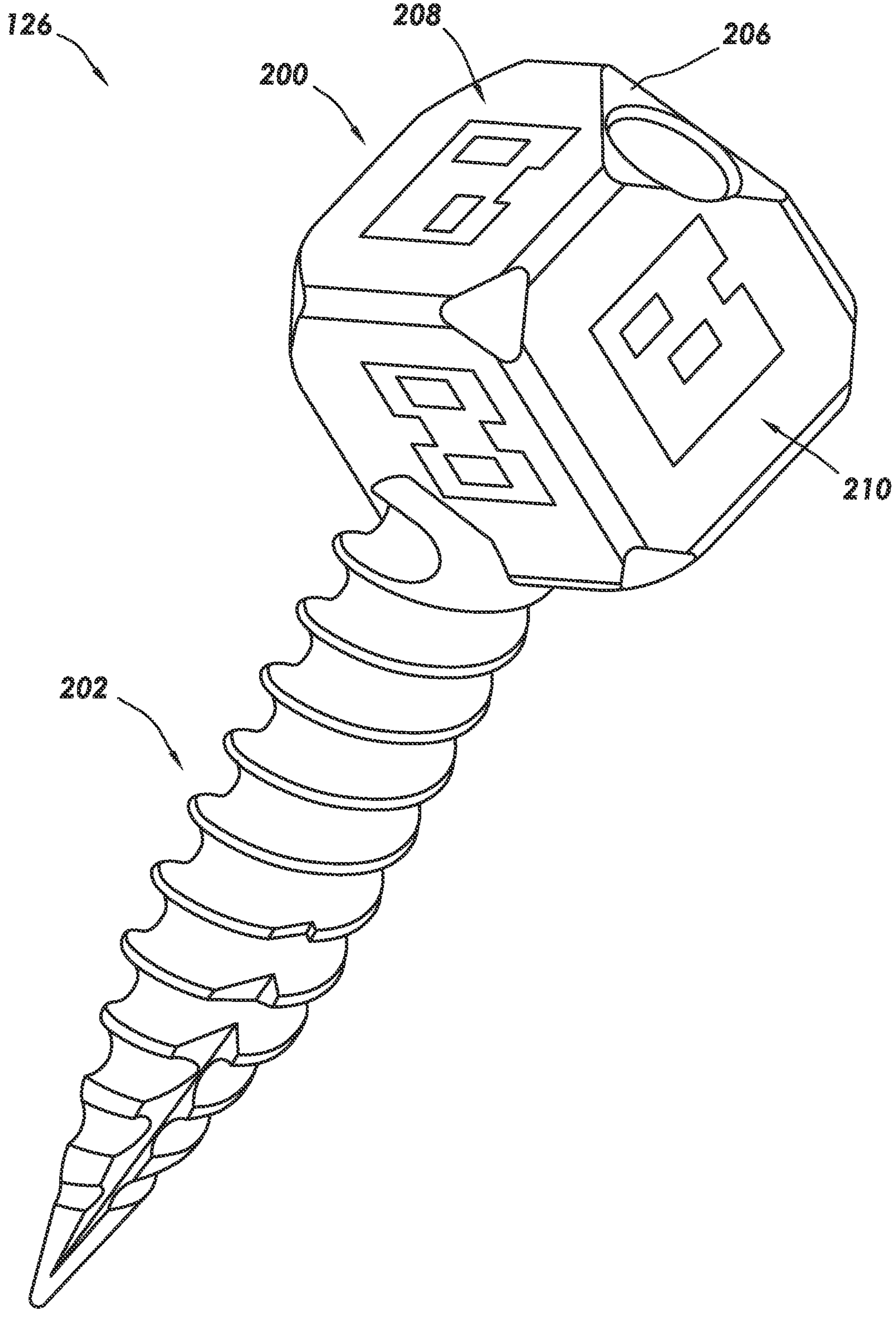
FIG. 18 shows a perspective side view of another example bone marker.

FIG. 18 shows a perspective side view of another example bone marker 126. In particular, the example bone marker 126 comprises a polyhedron 200 and an externally-threaded screw 202. The bone marker 126 of FIG. 18 is shown without a flange, but nevertheless may be used with flange as desired. The example polyhedron 200 defines an upper surface or upper face 206, and a plurality of outward-facing surfaces, such as outward-facing surface 208 and outward-facing surface 210. In the example of FIG. 18, the polyhedron 200 is a cube, but in this case the cube is tilted and the externally-threaded screw 202 extends from a “corner” of the cube. Each of the outward-facing surfaces, such as outward-facing surfaces 208 and 210 visible in FIG. 18, have disposed thereon a fiducial pattern.

In the example, the externally-threaded screw 202 projects from a side of the polyhedron 200 opposite from the upper face 206. Stated otherwise, a longitudinal central axis of the externally-threaded screw 202 extends through two opposite or opposing corners of the example cube. As before, in example cases the polyhedron 200 and the externally-threaded screw 202 are a monolithic structure, such as a continuous piece of metallic material (e.g., aluminum, stainless steel, titanium). The example externally-threaded screw 202 is a self-drilling or self-tapping screw. Again as before, the bone marker 126 of FIG. 18 is a relatively small object-in one example the outside diameter of the externally-threaded screw 202 is about 2.5 millimeters (mm)-though larger and smaller sizes are contemplated. In example cases, the polyhedron 200 may form faces that are about 4 mm in length (measured parallel to the longitudinal central axis 220). The overall length of example bone markers may be from 10 mm to 15 mm, inclusive, and in one example 12 mm.

Figure 19:
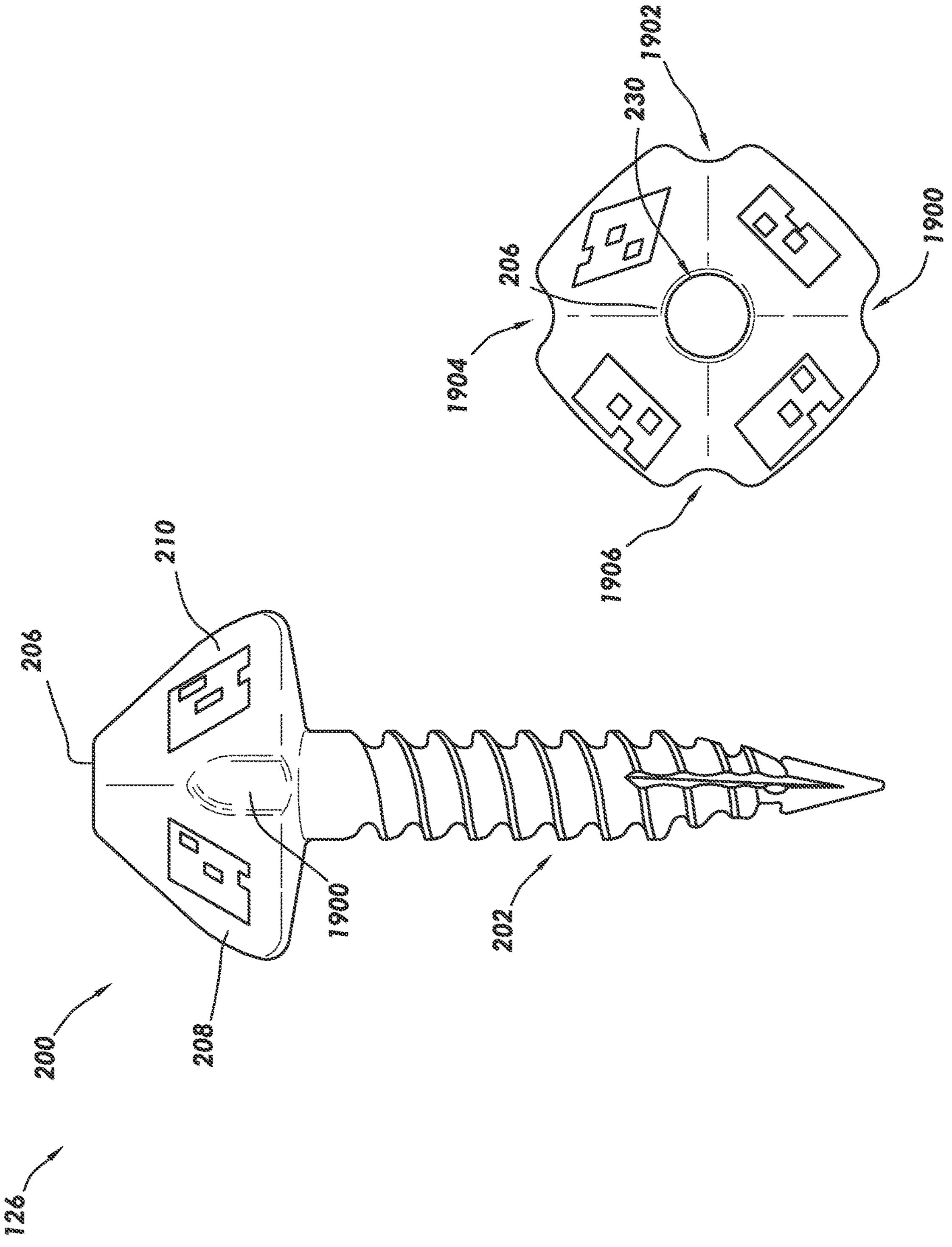
FIG. 19 shows a perspective side view of another example bone marker.

FIG. 19 shows a perspective side view of another example bone marker 126. In particular, the left portion of FIG. 19 shows a side-elevation view, while the right side of FIG. 19 shows a top view. The example bone marker 126 of FIG. 19 likewise comprises a polyhedron 200 and an externally-threaded screw 202. The bone marker 126 of FIG. 19 is shown without a flange, but nevertheless may be used with flange as desired. The example polyhedron 200 defines an upper surface or upper face 206, and a plurality of outward-facing surfaces, such as outward-facing surface 208 and outward-facing surface 210. In the example of FIG. 19, the polyhedron 200 is a hexahedron. Each of the outward-facing surfaces, such as outward-facing surfaces 208 and 210 visible in FIG. 19, have disposed thereon a fiducial pattern.

In the example, the externally-threaded screw 202 projects from a bottom side of the hexahedron opposite from the upper face 206. Stated otherwise, a longitudinal central axis of the externally-threaded screw 202 extends through the bottom of the hexahedron. As before, in example cases the polyhedron 200 and the externally-threaded screw 202 are a monolithic structure, such as a continuous piece of metallic material (e.g., aluminum, stainless steel, titanium). The example externally-threaded screw 202 is a self-drilling or self-tapping screw. Again as before, the bone marker 126 of FIG. 19 is a relatively small object—in one example the outside diameter of the externally-threaded screw 202 is about 2.5 millimeters (mm)—though larger and smaller sizes are contemplated. In example cases, the polyhedron 200 may form faces that are about 4 mm in length (measured parallel to the longitudinal central axis 220). The overall length of example bone markers may be from 10 mm to 15 mm, inclusive, and in one example 12 mm.

In the example shown in FIG. 19, the hexahedron may be associated with notches at the lower corners, such as notches 1900, 1902, 1904, and 1906. Each notch may define a closed bottom, and open top, and a notch axis. In the example shown, the notch axes may be parallel to each other and to the central axis (not specifically shown) of the externally-threaded threaded 202. The notches may be used by an installation tool (not specifically shown) to be the location at which the rotational installation force is imparted to the bone marker 126 of FIG. 19. Finally, and as before, the upper face 206 may associated with a retention bore 230 having a retention feature (not specifically shown in FIG. 19) disposed therein, the retention feature in any of the various forms discussed above.

In the various example bone markers discussed to this point, the flange (if present) is described as a separate and distinct component from the polyhedron and externally-threaded screw protruding therefrom. However, in yet still further examples the flange may be an integral component with the polyhedron and the externally-threaded screw, and in example cases the flange may be monolithic with the polyhedron and externally-threaded screw.

Figure 8:
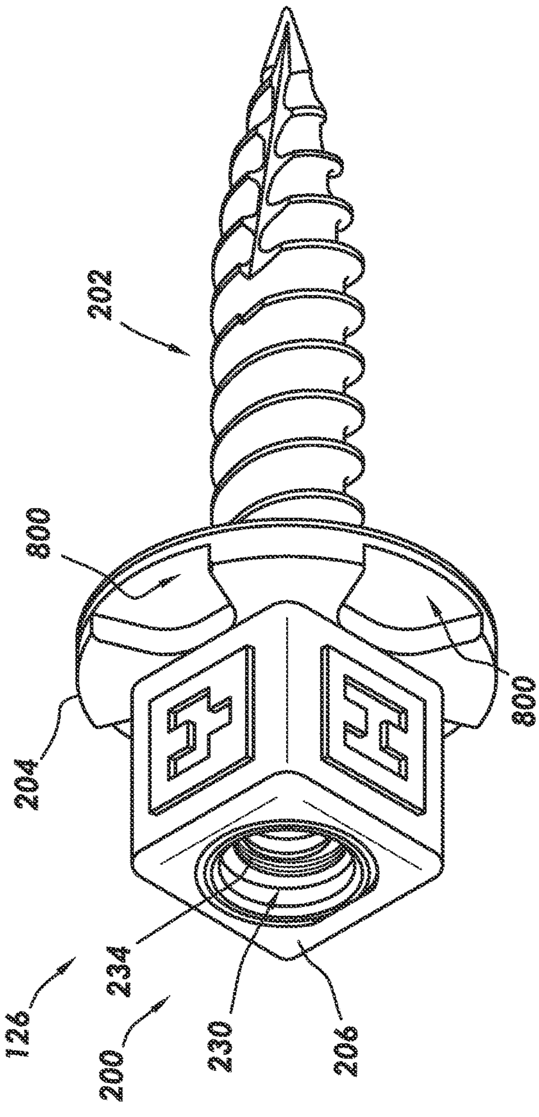
FIG. 8 shows a perspective view of a bone marker in accordance with at least some embodiments.

FIG. 8 shows a perspective view of an example bone marker 126. In particular, the example bone marker 126 of FIG. 8 comprises the polyhedron 200 and externally-threaded screw 202. As with the prior examples, the polyhedron 200 defines an upper face 206 having a retention bore 230 defined therein, including an example retention feature 234 in the form of threads. Further as before, the externally-threaded screw 202 projects from a side of the polyhedron 200 opposite from the upper face 206. And further as before, the flange 204 is disposed proximate to the intersection of the polyhedron 200 and the proximal end of the externally-threaded screw 202. In the example of FIG. 8 however, the flange 204 is an integral component with the externally-threaded screw 202. Thus, the flange 204 is rigidly coupled to the polyhedron and externally-threaded screw 202. In some cases, the polyhedron 200, the flange 204, and the externally-threaded screw 202 are a monolithic structure, such as a continuous piece of metallic material (e.g., aluminum). For example, the polyhedron 200, the flange 204, and the externally-threaded screw 202 may be simultaneously cast within a mold, or may be milled from single piece of aluminum. The example flange 204 nevertheless may capture or trap tissue against the bone beneath the flange 204 to reduce occurrences of debris and/or tissue obscuring fiducial patterns associated with the polyhedron 200. The example bone marker 126 of FIG. 8 may find beneficial use when the underlying bone is relatively flat or the bone slopes away from the point of attachment. For example, the bone marker 126 of FIG. 8 may be find beneficial use during treatment of femora-acetabular impingement when the bone marker 126 is placed on the anterior superior iliac spine of the pelvis.

Moreover, the example flange 204 of FIG. 8 may be the location at which rotational force is provided to install the bone marker 126 within the bone. To that end, the example flange 204 of FIG. 8 defines a plurality of indentions or notches 800 on the surface of the flange 204. An installation tool (not shown) may thus be designed and constructed to telescope over the polyhedron 200 and interact with the notches 800. Applying rotational force for installation at the notches 800 reduces the chances of damage to the fiducial patterns on the outward-facing surfaces of the polyhedron 200. However, applying rotational force for installation at the notches 800 may also increase the diameter of the distal end of the installation tool. The notches 800 are merely an example of a feature associated with the flange 204 to which the installation tool may couple for providing rotational force for installation and retrieval of the bone marker 126; however, the notches 800 may take any suitable form, such as: one or more counterbores of any suitable shape, the counterbores disposed at locations on the flange 204 that do not intersect the outside surface of the flange 204; and one or more throughbore of any suitable shape, the throughbores disposed at locations on the flange 204 that do not intersect the outside surface of the flange 204.

In the example of FIG. 8, the polyhedron 200 may be a separate component from the externally-threaded screw 202 and the flange 204. In particular, the example bone marker 126 of FIG. 8 may comprise a tube or nipple extending proximally from the flange 204, with an inside surface of the nipple forming the retention bore 230 and retention feature 234. Thus, the nipple, the flange 204, and the externally-threaded screw 202 may be a monolithic component (e.g., metallic), while the polyhedron 200 may be a separate and distinct component (e.g., polymeric material, such as plastic) telescoped over the nipple during assembly of the bone marker 126. It follows, using the flange 204 as the mechanical structure to which rotational force for installation is applied enables making the polyhedron from different materials, possibly using different and less expensive construction techniques.

Figure 9:
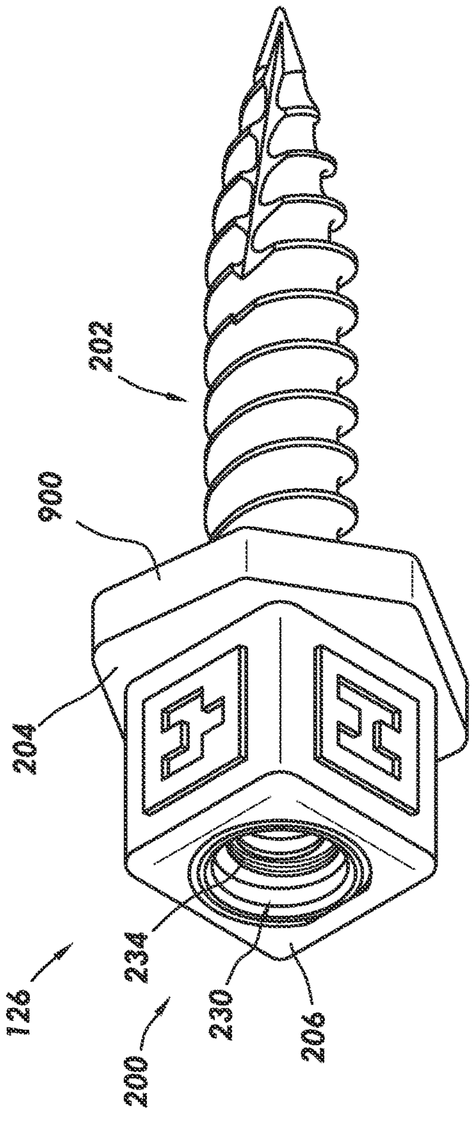
FIG. 9 shows a perspective view of a bone marker in accordance with at least some embodiments.

FIG. 9 shows a perspective view of an example bone marker 126. In particular, the example bone marker 126 of FIG. 9 comprises the polyhedron 200 and externally-threaded screw 202. As with the prior examples, the polyhedron 200 defines an upper face 206 having the retention bore 230 defined therein, including an example retention feature 234 in the form of threads. Further as before, the externally-threaded screw 202 projects from a side of the polyhedron 200 opposite from the upper face 206. And further as before, the flange 204 is disposed proximate to the intersection of the polyhedron 200 on the proximal end of the externally-threaded screw 202. In the example of FIG. 9 the flange 204 is an integral component of the bone marker 126. Thus, the flange 204 is rigidly coupled to the polyhedron and externally-threaded screw 202. In some cases, the polyhedron 200, the flange 204, and the externally-threaded screw 202 are a monolithic structure, such as a continuous piece of metallic material (e.g., aluminum). As before, the example flange 204 may capture or trap tissue against the bone beneath the flange 204 to reduce occurrences of debris and/or tissue obscuring fiducial patterns associated with the polyhedron 200. As with the bone marker of FIG. 8, the example bone marker 126 of FIG. 9 may find beneficial use when the underlying bone is relatively flat or the bone slopes away from the point of attachment.

Moreover, the example flange 204 of FIG. 9 may be the location at which rotational force is provided to install the bone marker 126 within the bone. To that end, an outside surface of the example flange 204 of FIG. 9 defines a hexagon. An installation tool (not shown) may thus be designed and constructed to telescope over the polyhedron 200 and telescope over and interact with the hexagonal outside surface 900. Applying rotational force for installation at the hexagonal outside surface 900 reduces the chances of damage to the fiducial patterns on the outward-facing surfaces of the polyhedron 200. However, applying rotational force for installation at the hexagonal outside surface 900 may also increase the diameter of the distal end of the installation tube. The hexagonal outside surface 900 are merely an example of a feature to which the installation tool may couple for providing rotational force for installation and retrieval of the bone marker 126.

Again in the example of FIG. 9, the polyhedron 200 may be a separate component from the externally-threaded screw 202 and the flange 204. In particular, the example bone marker 126 of FIG. 9 may comprise a tube or nipple extending proximally from the flange 204, with an inside surface of the nipple forming the retention bore 230 and retention feature 234. The nipple, the flange 204, and the externally-threaded screw 202 may be a monolithic component (e.g., metallic), while the polyhedron 200 may be a separate and distinct component (e.g., polymeric material, such as plastic). Thus again, using the flange 204 as the mechanical structure to which rotational force for installation is applied enables making the polyhedron from different materials. The specification now turns to other examples of method and systems to reduce debris and/or tissue obscuring the fiducial patterns, in the example context of an aimer.

Figure 10:
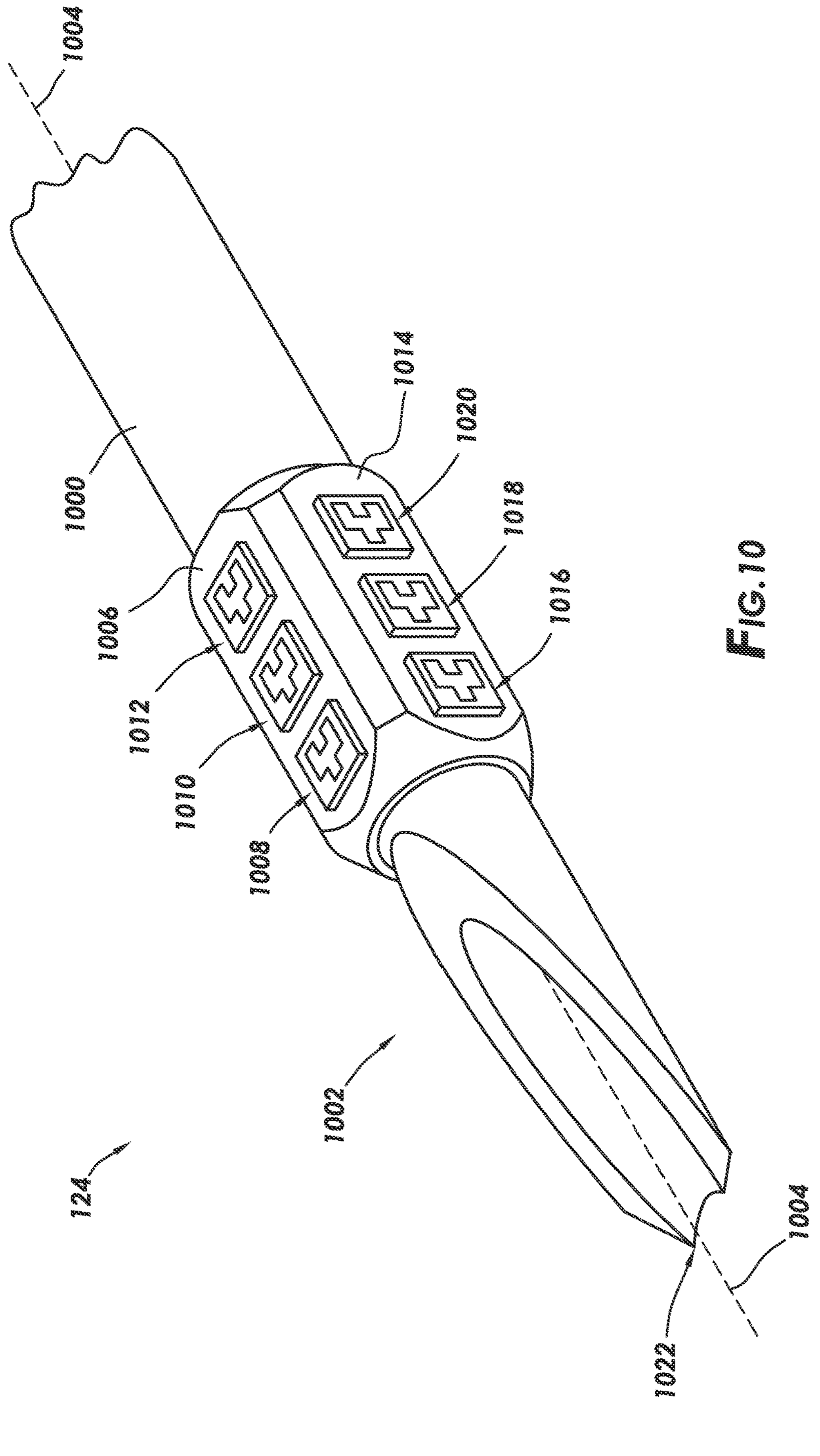
FIG. 10 shows a perspective view of a distal end of an aimer in accordance with at least some embodiments.

FIG. 10 shows a perspective view of a distal end of the example aimer 124. In particular, FIG. 10 shows the example aimer 124 comprises an elongate shaft 1000 defining the distal end 1002, a proximal end (not visible), and a longitudinal central axis 1004. In the example aimer 124, the distal end 1002 is sharpened to a point help hold the aimer 124 in place against the bone during placement and drilling, but in other cases the sharped point may be omitted. In order for the surgical controller 118 (FIG. 1) to determine the location of the aimer 124 with the respect a bone visible in images as viewed by the arthroscope 108 (FIG. 1) and camera head 110 (FIG. 1), the example aimer 124 comprises a plurality of fiducial patterns associated with the aimer 124. More particularly, the example aimer 124 defines a fiducial surface 1006 disposed proximate to the distal end 1002. The fiducial surface 1006 comprises a plurality of fiducial patterns thereon at varying axial positions. For example, the fiducial surface 1006 comprises a distal fiducial pattern 1008, a medial fiducial pattern 1010, and a proximal fiducial pattern 1012. The distal fiducial pattern 1008 is at a distal axial position along the longitudinal central axis 1004. The medial fiducial pattern 1010 is disposed proximally from the distal fiducial pattern 1008. The proximal fiducial pattern 1012 is disposed proximally from the medial fiducial pattern 1010. While three fiducial patterns are shown associated with the fiducial surface 1006, two or more fiducial patterns may be implemented on the fiducial surface 1006 to reduce occurrences of debris and/or tissue obscuring fiducial patterns during arthroscopic surgical procedures. In some cases, the fiducial surface 1006 defines a plane upon which the fiducial patterns are created or attached. Having the fiducial surface 1006 define a plane provides additional straight-line features upon which the surgical controller 118 may rely in determining the orientation of the fiducial patterns. However, in yet still other cases the fiducial surface need not be planar, and may take other suitable shapes (e.g., cylindrical).

In some surgical procedures, the relationship between the fiducial surface 1006 and a viewing angle of the arthroscope 108 (FIG. 1) may be such that the fiducial surface 1006 is always in the view of the arthroscope 108. However, in other surgical procedures (e.g., ACL replacement), the rotational orientation of the aimer 124 relative to the view of the arthroscope 108 may not be guaranteed. Thus, in yet still further cases the example aimer 124 comprises additional fiducial surfaces, with each additional fiducial surface likewise having a plurality of fiducial patterns. In particular, FIG. 10 shows another fiducial surface 1014 that comprises a distal fiducial pattern 1016, a medial fiducial pattern 1018, and a proximal fiducial pattern 1020. The example aimer 124 comprises four fiducial surfaces, though in the view of FIG. 10 only the fiducial surfaces 1006 and 1014 are visible. When four fiducial surfaces are implemented, the fiducial surfaces may define planes that are perpendicular to the planes defined by adjoining fiducial surfaces. For example, fiducial surface 1006 defines a plane that is perpendicular to a plane defined by fiducial surface 1014. The example four fiducial surfaces form an exterior surface around the outer surface of the elongate shaft 1000, and thus an exterior surface around the longitudinal central axis 1004.

Having four fiducial surfaces forming an exterior surface around the longitudinal central axis 1004 is merely an example. In other cases, fewer than four fiducial surfaces may be used. For example, three fiducial surfaces may be used, and those three fiducial surfaces may form an exterior surface around the longitudinal central axis 1004. Further still, the fiducial surfaces need not form an exterior surface that fully surrounds the longitudinal central axis 1004. For example, if the view of the arthroscope can be relatively assured to be in a range of rotational orientations with the respect to the longitudinal central axis 1004, one or more of the fiducial surfaces and its respective fiducial patterns may be omitted (e.g., the fiducial surface on the back side of the object).

In the example aimer 124, the fiducial pattern 1008 is at the same axial position as the fiducial pattern 1016, but at different radial locations relative to the longitudinal central axis 1004. For the fiducial surfaces not visible in FIG. 10, distal fiducial patterns may likewise be at the same axial positions as the fiducial patterns 1008 and 1016, but again each at a distinct radial location relative to the longitudinal central axis 1004. Similarly, the fiducial pattern 1010 is at the same axial position as the fiducial pattern 1018, but at different radial locations relative to the longitudinal central axis 1004. The medial fiducial patterns on the fiducial surfaces not visible may be at the same axial position. The fiducial pattern 1012 is at the same axial position as the fiducial pattern 1020, but at different radial locations relative to the longitudinal central axis 1004. The proximal fiducial patterns on the fiducial surfaces not visible may be at the same axial position. In yet still other examples, the axial positions of the fiducial patterns as between fiducial surfaces need not be the same.

Still referring to FIG. 10, for the example aimer 124 the fiducial surfaces (e.g., 1006, 1014) may be constructed and associated with the elongate shaft 1000 in any suitable way. For example, in some cases the fiducial surfaces and respective fiducial patterns may be a monolithic with the elongate shaft 1000. In other cases, the fiducial surfaces and respective fiducial patterns may be a separate and distinct component telescoped over the elongate shaft 1000. For example, the fiducial surfaces and respective fiducial patterns may be part of a fiducial assembly that defines a throughbore. The fiducial assembly may be telescoped over the elongate shaft 1000, with the inside diameter of the throughbore designed and constructed to form a friction fit with the outside surface of the elongate shaft 1000. Thus, the fiducial assembly may be a disposable element made of a polymeric material (e.g., plastic), and the underlying aimer 124 may be metallic and thus sterilized by autoclave.

The operative information regarding the aimer 124 is the orientation of the longitudinal central axis 1004 relative to the other objects in the images captured by the arthroscope 108 (FIG. 1) and camera head 110 (FIG. 1). That is, if the surgical controller 118 (FIG. 1) can determine the orientation of the longitudinal central axis 1004 in the three-dimensional coordinate space of the view of the arthroscope 108, no further spatial relationship may be needed. For example, once the surgical controller 118 knows the orientation of the longitudinal central axis 1004, the orientation of the aimer 124 relative to other tracked objects (e.g., bone) can be determined. It follows that, for the aimer 124, the precise location of the distal tip 1022 need not be defined relative to the fiducial patterns. For that reason, the fiducial patterns neither need to be distinct along a fiducial surface, nor do the fiducial patterns need to be distinct amongst the fiducial surfaces. Stated otherwise, when only the orientation of the longitudinal central axis 1004 is of interest, all the fiducial patterns may be identical, as shown in FIG. 10. For other medical instruments, such as the touch probe 122 (FIG. 2), the precise location of the distal tip may need be known.

Figure 11:
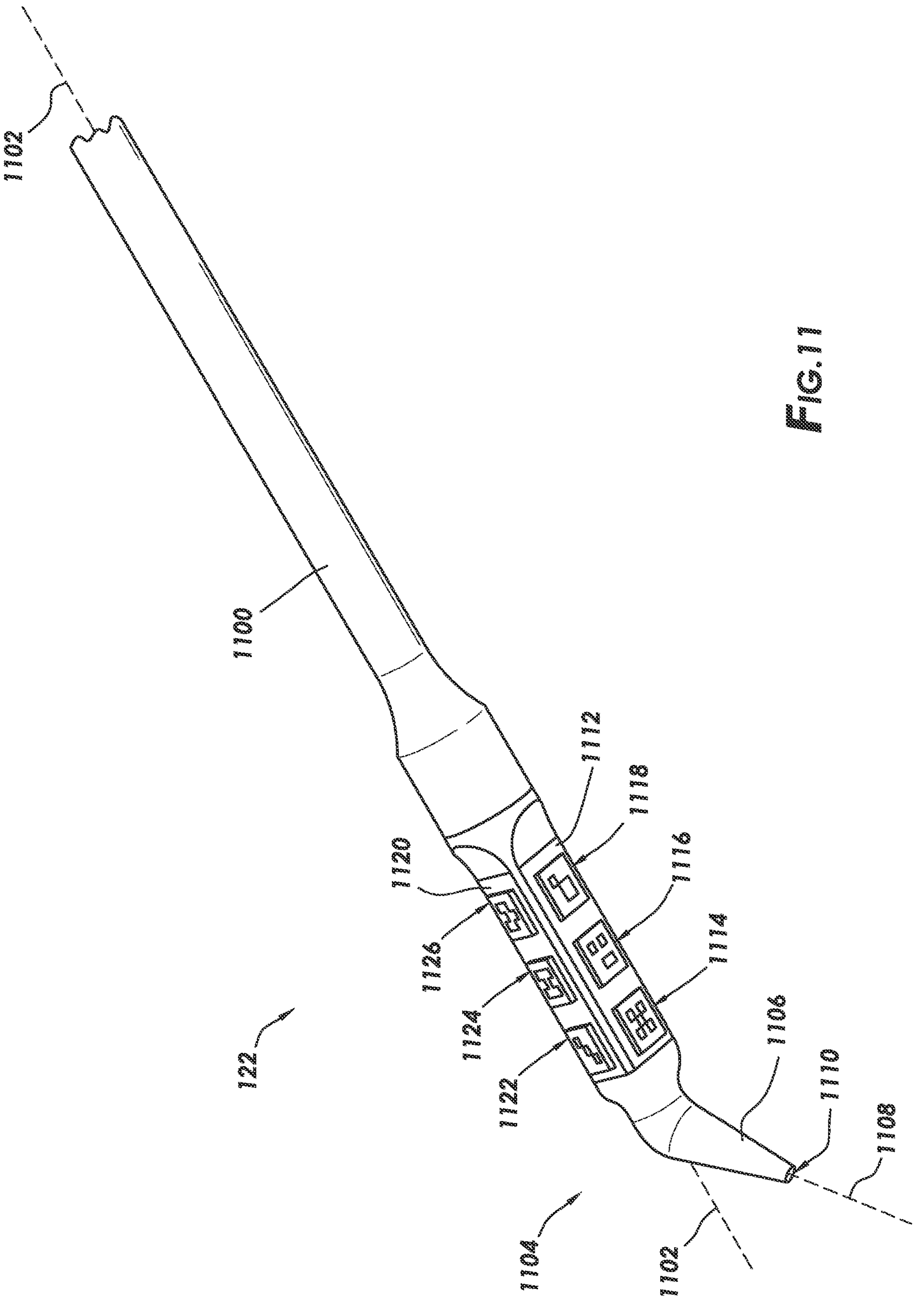
FIG. 11 shows a perspective side view of a touch probe in accordance with at least some embodiments.

FIG. 11 shows a perspective side view of a distal end of an example touch probe 122. In particular, FIG. 11 shows the example touch probe 122 comprises an elongate shaft 1100, a proximal end (not visible), and a longitudinal central axis 1102. The example touch probe 122 has a distal end 1104 that comprises a probe end 1106 comprising a probe axis 1108. In the example case, the probe end 1106 defines a conic frustum with a narrow distal end rounded to form a touch surface 1110, and a wider proximal end closer to the longitudinal central axis 1102. In example cases, the probe axis 1108 forms an acute angle with the longitudinal central axis 1102, the acute angle measured beyond the distal end 1104 of the touch probe 122. In use, the touch surface 1110 is touched against the bone to provide location information to the surgical controller 118 (FIG. 1), such as to provide data to register a three-dimensional bone model to the bone, or to provide revised-tunnel entry locations and revised-tunnel exit locations during intraoperative tunnel path changes.

In order for the surgical controller 118 (FIG. 1) to determine the location of the touch surface 1110 with the respect a bone visible in images as viewed by the arthroscope 108 (FIG. 1) and camera head 110 (FIG. 1), the example touch probe 122 comprises a plurality of fiducial patterns associated with the touch probe 122. More particularly, the example touch probe 122 defines a fiducial surface 1112 disposed proximate to the touch surface 1110. The fiducial surface 1112 comprises a plurality of fiducial patterns thereon at varying axial positions relative to the longitudinal central axis 1102. For example, the fiducial surface 1112 comprises a distal fiducial pattern 1114, a medial fiducial pattern 1116, and a proximal fiducial pattern 1118. The distal fiducial pattern 1114 is at a distal axial position along the longitudinal central axis 1102. The medial fiducial pattern 1116 is disposed proximally from the distal fiducial pattern 1114. The proximal fiducial pattern 1118 is disposed proximally from the medial fiducial pattern 1116. While three fiducial patterns are shown associated with the fiducial surface 1112, two or more fiducial patterns may be implemented on the fiducial surface 1112 to reduce occurrences of debris and/or tissue obscuring fiducial patterns during arthroscopic surgical procedures. In some cases, the fiducial surface 1112 defines a plane upon which the fiducial patterns are created or attached. Having the fiducial surface 1112 define a plane provides additional straight-line features upon which the surgical controller 118 may rely in determining the orientation of the fiducial patterns. However, in yet still other cases the fiducial surface need not be planar, and may take other suitable shapes (e.g., cylindrical).

In some surgical procedures, the relationship between the fiducial surface 1112 and a viewing angle of the arthroscope 108 (FIG. 1) may be such that the fiducial surface 1112 is always in the view of the arthroscope 108. More likely, however, is that the rotational orientation of the touch probe 122 may vary significantly during the intraoperative procedure. Thus, in yet still further cases the example touch probe 122 comprises additional fiducial surfaces, with each additional fiducial surface likewise having a plurality of fiducial patterns. In particular, FIG. 11 shows another fiducial surface 1120 that comprises a distal fiducial pattern 1122, a medial fiducial pattern 1124, and a proximal fiducial pattern 1126. The example touch probe 122 comprises three fiducial surfaces, though in the view of FIG. 11 only the fiducial surfaces 1112 and 1120 are visible. The example three fiducial surfaces form an exterior surface around the longitudinal central axis 1102. In other cases, the fiducial surfaces need not form an exterior surface that fully surrounds the longitudinal central axis 1102.

In the example touch probe 122, the fiducial pattern 1114 is at the same axial position as the fiducial pattern 1122, but at different radial locations relative to the longitudinal central axis 1102. For the fiducial surface not visible in FIG. 11, the distal fiducial pattern may likewise be at the same axial position as the fiducial patterns 1114 and 1122, but again each at a distinct radial location relative to the longitudinal central axis 1102. Similarly, the fiducial pattern 1116 is at the same axial position as the fiducial pattern 1124, but at different radial locations relative to the longitudinal central axis 1102. The medial fiducial pattern on the fiducial surface not visible may be at the same axial position. The fiducial pattern 1118 is at the same axial position as the fiducial pattern 1126, but at different radial locations relative to the longitudinal central axis 1102. The proximal fiducial pattern on the fiducial surface not visible may be at the same axial position. In yet still other examples, the axial positions of the fiducial patterns as between fiducial surfaces need not be the same.

The operative information regarding the touch probe 122 is the location of the touch surface 1110 relative to the other objects in the images captured by the arthroscope 108 (FIG. 1) and camera head 110 (FIG. 1). Because of the offset of the touch surface 1110 from the longitudinal central axis 1102 (the offset measured perpendicular to the longitudinal central axis 1102), the straight line distances between each fiducial pattern and the touch surface 1110 are different. For example, the distance between the fiducial pattern 1118 and the touch surface 1110 is greater than the distance between the fiducial pattern 1114 and the touch surface 1110. Similarly, the distance between the fiducial pattern 1126 and the touch surface 1110 is greater than the distance between the fiducial pattern 1122 and the touch surface 1110. Further still, the straight line distance between the fiducial pattern 1126 and the touch surface 1110 is different than the straight line distance between the fiducial pattern 1118 and the touch surface 1110. Because the distance between each fiducial pattern and the touch surface 1110 is different, each fiducial pattern implemented may be distinct and unique with respect all the other fiducial patterns implemented by the touch probe 122. Thus, the surgical controller 118 (FIG. 1) determines the location of the touch surface 1110 in the three-dimensional coordinate space of the view of the arthroscope 108 by reading at least one of the fiducial patterns visible in the images received. When debris and/or tissue block one or more of the fiducial patterns, the surgical controller 118 may nevertheless determine the location of the touch surface 1110 based on the one or more fiducial patterns still visible. The specification addresses in greater detail below an example of how the surgical controller selects a particular fiducial pattern when more than one fiducial pattern is visible in the images.

Figure 12:
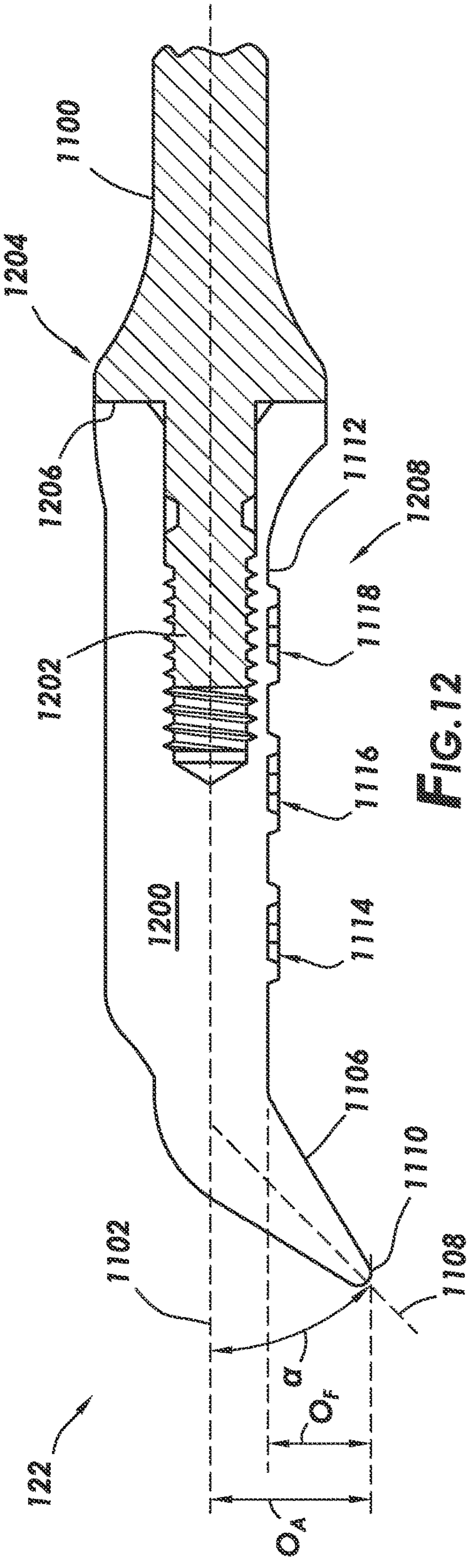
FIG. 12 shows a cross-sectional view of a distal end of a touch probe in accordance with at least some embodiments.

FIG. 12 shows a cross-sectional view of the example touch probe 122, the cut for the view FIG. 12 taken along the longitudinal central axis 1102 and through the middle of the fiducial surface 1112. In particular, visible in FIG. 12 are the elongate shaft 1100, the probe end 1106, the touch surface 1110, the probe axis 1108, the fiducial surface 1112, the distal fiducial pattern 1114, the medial fiducial pattern 1116, and the proximal fiducial pattern 1118. Because in the example touch probe 122 three fiducial surfaces are used, the cross-sectional view only shows the fiducial surface 1112.

The example touch probe 122 comprises at least two components: the elongate shaft 1100; and a probe assembly 1200. In particular, the example elongate shaft 1100 defines a threaded stem 1202 protruding along the longitudinal central axis 1102. Further, the elongate shaft 1100 defines a flange region 1204 having an outside diameter larger than the outside diameter of the elongate shaft 1100. The flange region 1204 defines a shoulder 1206 disposed between an outside diameter of the threaded stem 1202 and the outside diameter of the flange region 1204. The interface between the probe assembly 1200 and the shoulder 1206 may be used to increase the force needed to unscrew the probe assembly 1200 from the threaded stem 1202, so as to reduce the chance of probe assembly 1200 becoming loose during the intraoperative procedure.

The probe end 1106 extends away from the longitudinal central axis 1102 at an acute angle α measured distally from the touch probe 122. Moreover, the touch surface 1110 has an offset $O_A$ measured perpendicularly from the longitudinal central axis 1102. And the touch surface 1110 has an offset $O_F$ from the fiducial surface 1112 (again measured perpendicularly from the longitudinal central axis 1102). In various examples, the offsets $O_A$ and $O_F$ are designed and constructed such that the probe assembly 1200 defines a notch region 1208. The notch region 1208 may enable the surgeon to reach "around" various objects within the surgical field and nevertheless touch bone surface. In one example, the offset $O_A$ is about 7 mm, the offset $O_F$ is about 5 mm, and the outside diameter of the flange region 1205 is about 10 mm. Thus, notch region 1208 enables the offset $O_F$ of about 5 mm while maintaining the displacement of the probe end 1106 to be only about 2 mm beyond the outside diameter of the flange region 1204.

In the example touch probe 122 of FIG. 12, the probe assembly 1200 has a counter bore defining internal threads that couple to the external threads on threaded stem 1202. However, the mechanical arrangement is merely an example. Other examples include the probe assembly 1200 defining a threaded stem that protrudes proximally, and the elongate shaft 1100 defining a counterbore having internal threads, and into which the threaded stem of the probe assembly is coupled. Further still, the probe assembly 1200 may itself be a two-piece component, with the probe end 1106 defining a threaded stem that is coupled to the elongate shaft, and the fiducial surfaces being a member with a throughbore telescoped over the threaded stem. Another example is a one piece shaft with reduced diameter distal portion including the tip. A triangular fiducial section is slid over the reduced diameter section and rotationally keyed to the shaft. The reduced diameter section protruding distally from the fiducials is finally bent at the angle α. Many variations are possible.

Figure 13:
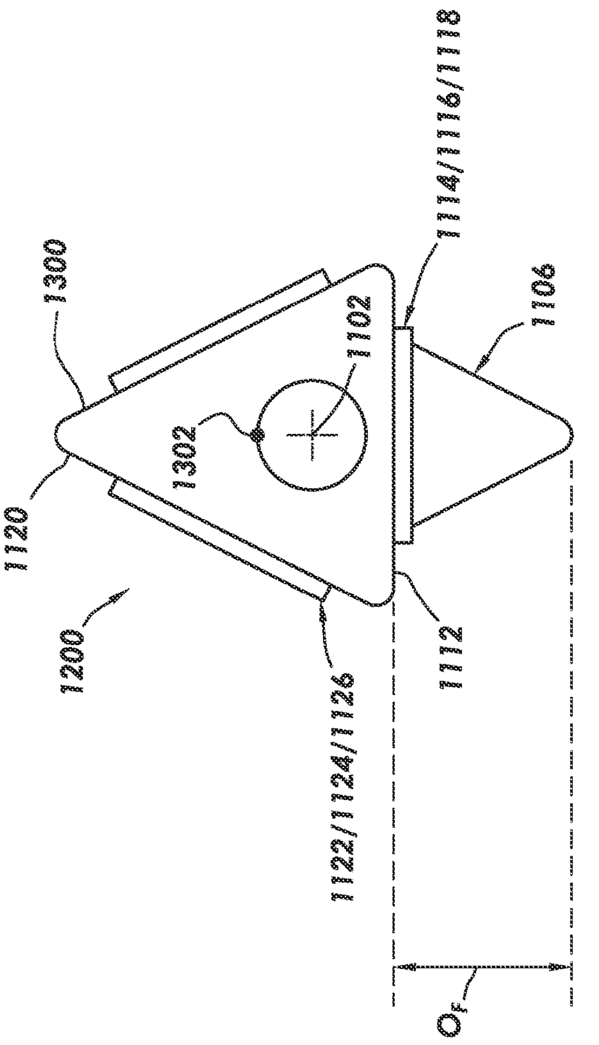
FIG. 13 shows a cross-sectional elevation view taken through the probe assembly and looking distally, and in accordance with at least some embodiments.

FIG. 13 shows a cross-sectional elevation view taken through the probe assembly 1200 and looking distally toward the probe end 1106. In particular, FIG. 13 shows a cross-section of a probe assembly 1200 illustratively comprising the fiducial surface 1112, the fiducial surface 1120, and a third fiducial surface 1300. In the example, the fiducial surfaces 1112, 1120, and 1300 form an exterior surface around the longitudinal central axis 1102 (in the view of FIG. 13, the longitudinal central axis 1102 is perpendicular to the plane of the page, and thus shown as a dot). The exterior surface formed is triangular in spite the rounded or curved corners between the fiducial surfaces. In the cross-section, also visible is a portion of a fiducial pattern on the fiducial surface 1120, which could be any of the fiducial patterns 1114, 1116, or 1118. Further in the cross-section, also visible is a portion of a fiducial pattern on the fiducial surfaces 1120, which could be any of the fiducial patterns 1122, 1124, or 1126. In example cases, the fiducial surface 1300 likewise would have three fiducial patterns, and the view of FIG. 13 could be any of those three fiducial patterns.

In the example triangular probe assembly 1200, the cross-section of the triangular portion defines a geometric center 1302. Stated otherwise, the triangular portion of probe assembly 1200 defines a longitudinal central axis, which in the view of FIG. 13 is perpendicular to the plane of page and thus shown as geometric center 1302. In example cases the geometric center 1302 has a non-zero offset from the longitudinal central axis 1102. Stated another way, the fiducial surface 1112 is closer to the longitudinal central axis 1102 than the geometric center 1302, with both distances measured perpendicular to the longitudinal central axis 1102. The relationship of the fiducial surface 1112 to the longitudinal central axis 1102 and the offset $O_F$ create the notch region 1208 (FIG. 12).

The example bone marker 126, the aimer 124, and touch probe 122 all have multiple fiducial patterns. The fiducial patterns are spread radially around a longitudinal central axis of the object, and in the case of the aimer 124 and touch probe 122 fiducial patterns are spread axially along the longitudinal central axis. The objective is that during surgical procedures, at least one fiducial pattern should be visible even in the event that debris and/or tissue obscures some of the fiducial patterns. In many instances, however, the surgical controller 118 (FIG. 1) may see multiple fiducial patterns in the images captured by the arthroscope 108 (FIG. 1) and camera head 110 (FIG. 1). More particularly, the surgical controller 118 receives images as viewed by the arthroscope 108 and attached camera head 110 during a surgical procedure, the images including images of an instrument having a plurality of fiducials patterns. The surgical controller 118 then selects a non-obscured fiducial from the plurality of fiducial patterns that are visible in the images, and calculates a value indicative of location of the instrument within the surgical site based on the non-obscured fiducial pattern. The value indicative of location may take many forms. In the case of the bone marker 126, the value indicative of location may be a location in the three-dimensional coordinate space of the view of the arthroscope being an anchor location for a three-dimensional bone model previously registered to the bone marker 126. In the case of aimer 124, the value indicative of location may be an orientation of the longitudinal central axis of the aimer 124. In the case of the touch probe 122, the value indicative of location may be the location of the touch surface 1110 in the three-dimensional coordinate space of the view of the arthroscope.

Regardless of the precise value indicative of location calculated, in example systems the surgical controller 118 then performs an intraoperative task based on the value indicative of location. The intraoperative task may take many forms. For example, the surgical controller may register a location on a bone visible within the images, the location selected or designated by the touch probe 122. As another example, the surgical controller 118 may use the value indicative of location to select a revised-tunnel entry for a tunnel through a bone, or a location for a revised-tunnel exit for a tunnel through the bone. The value indicative of location in the form of the longitudinal central axis of the aimer 124 may be used to determine a location of a distal end of an aimer relative to a bone visible in the images and/or to determine relative orientation of the longitudinal central axis of the aimer 124 to a central axis of a planned tunnel through the bone.

Figure 14:
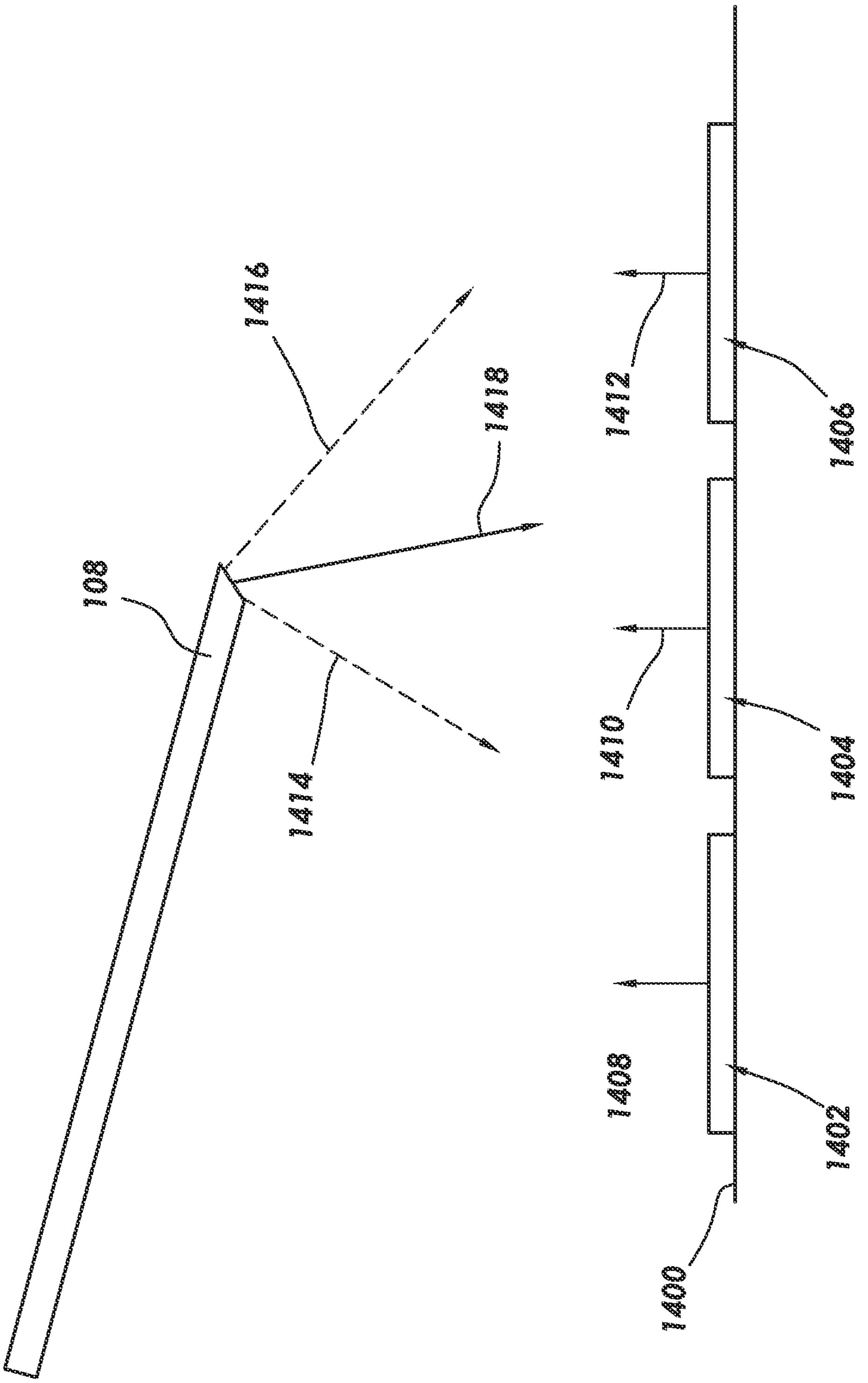
FIG. 14 shows a side elevation view of an arthroscope and a plurality of fiducial patterns in accordance with at least some embodiments.

FIG. 14 shows a side elevation view of an arthroscope 108 and a plurality of fiducial patterns in order to discuss selection of a fiducial pattern when more than one fiducial pattern is visible in the images received. In particular, FIG. 14 shows a fiducial surface 1400 comprising fiducial patterns 1402, 1404, and 1406. The view is a side elevation view, so the actual patterns of the fiducial patterns 1402, 1404, and 1406 are not visible in FIG. 14. Each fiducial pattern 1402, 1404, and 1406 defines a normal vector 1408, 1410, and 1412, respectively. In each case, the "normal vector" is a vector perpendicular to the outer face of the fiducial pattern, and in some cases perpendicular to the underlying fiducial surface 1400. The example arthroscope 108 defines a viewing angle bounded by example arrows 1414 and 1416. Further, the example arthroscope 108 defines a view direction 1418 being a vector subtending the viewing angle. In the example of FIG. 14, the fiducial pattern 1402 is not fully visible within the viewing angle of the arthroscope 108; however, fiducial patterns 1404 and 1406 are visible within the viewing angle.

The issue becomes selection of one of the non-obscured fiducial patterns 1404 or 1406 with which to do further processing. In example systems, the surgical controller 118 selects the non-obscured fiducial pattern whose normal vector is closest to coaxial with a view direction 1418 of the arthroscope 108. In the example of FIG. 14, the normal vector 1410 of the fiducial pattern 1404 is closest to coaxial with the view direction 1418, and thus while the both the fiducial patterns 1404 and 1406 are visible, the surgical controller 118 selects one with which to proceed. The example FIG. 14 is two dimensional—just the plane of the page. However, in practice the view direction 1418 of the arthroscope 108 may vary in three dimensions relative to the normal vectors of the visible fiducial patterns. Choosing a fiducial pattern whose normal vector is closest to the view direction may mean that an orientation of the fiducial pattern, and thus the underlying object, may have less uncertainty than, for example, a fiducial pattern viewed with a small acute angle (e.g., an angle between the viewing angle and the normal vector is large).

Figure 15:
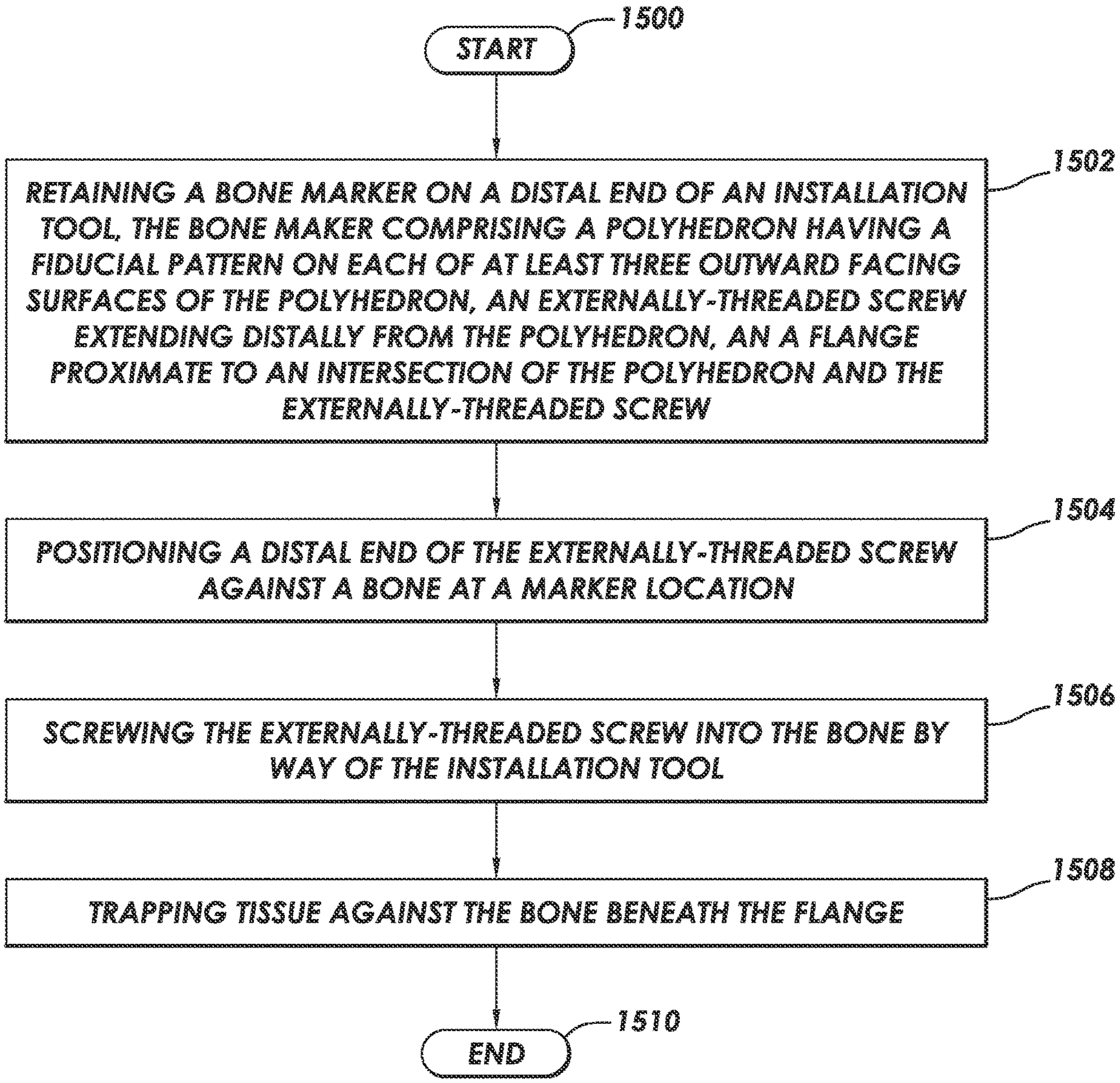
FIG. 15 shows a method in accordance with at least some embodiments.

FIG. 15 shows a method in accordance with at least some embodiments. In particular, the method starts (block 1500) and comprises: retaining a bone marker on a distal end of an installation tool, the bone marker comprising a polyhedron having a fiducial pattern on each of at least three outward facing surfaces of the polyhedron, an externally-threaded screw extending distally from the polyhedron, and a flange proximate to an intersection of the polyhedron and the externally-threaded screw (block 1502); positioning a distal end of the externally-threaded screw against a bone at a marker location (block 1504); screwing the externally-threaded screw into the bone by way of the installation tool (block 1506); and trapping tissue against the bone beneath the flange (block 1508). Thereafter, the example methods ends (block 1510).

Figure 16:
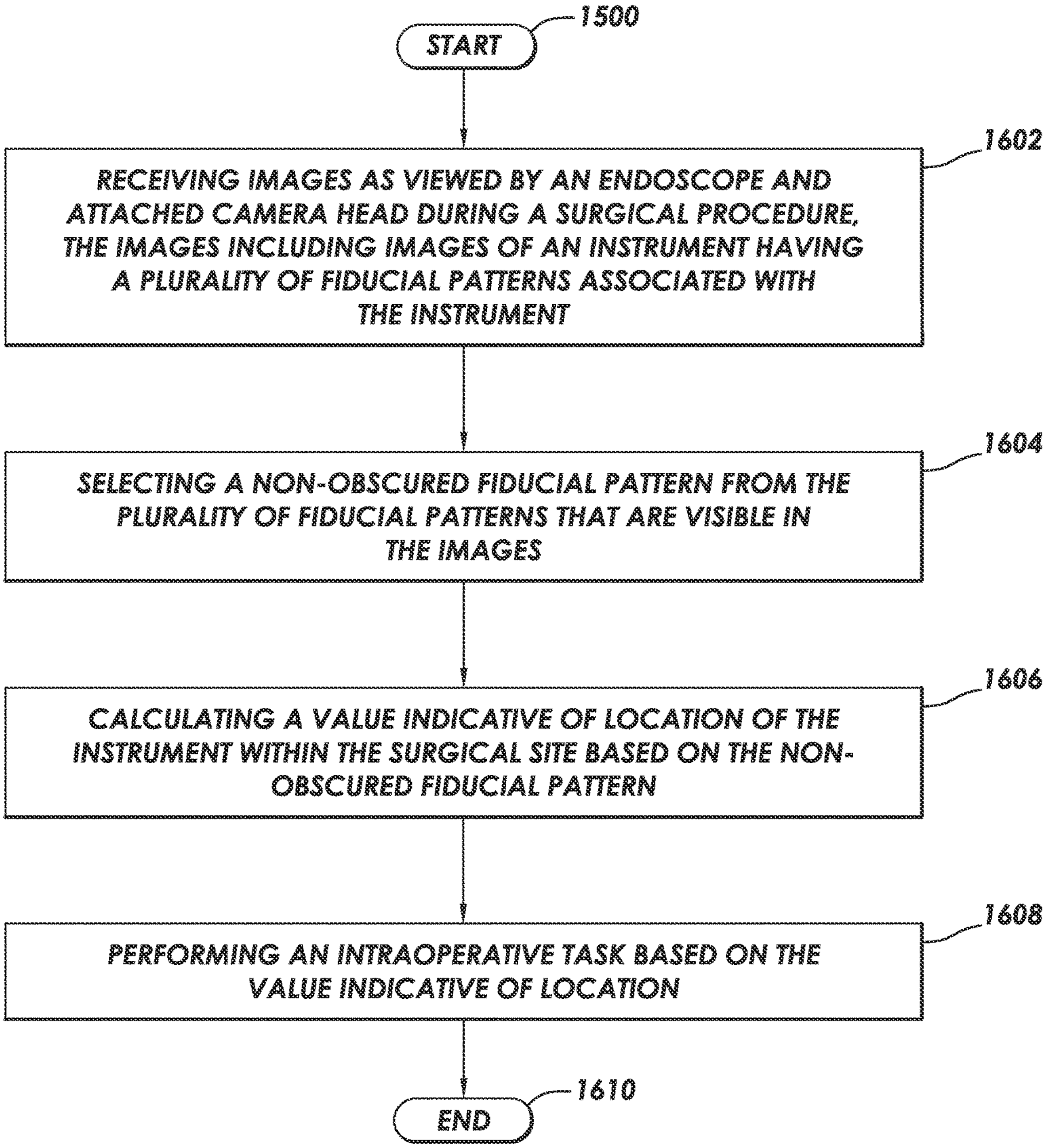
FIG. 16 shows a method in accordance with at least some embodiments.

FIG. 16 shows a method in accordance with at least some embodiments. In particular, the example method of FIG. 16 may be implemented, at least in part, by instructions executed by a processor within a computer system, such as the surgical controller 118 (FIG. 1). The example method starts (block 1600) and comprises: receiving images as viewed by an endoscope and attached camera head during a surgical procedure, the images including images of an instrument having a plurality of fiducials patterns associated with the instrument (1602); selecting a non-obscured fiducial pattern from the plurality of fiducial patterns that are visible in the images (1604); calculating a value indicative of location of the instrument within the surgical site based on the non-obscured fiducial pattern (block 1606); and performing an intraoperative tasked based on the value indicative of location (block 1608). Thereafter, the example methods ends (block 1610), likely to be restarted with a next set of images received.

Figure 17:
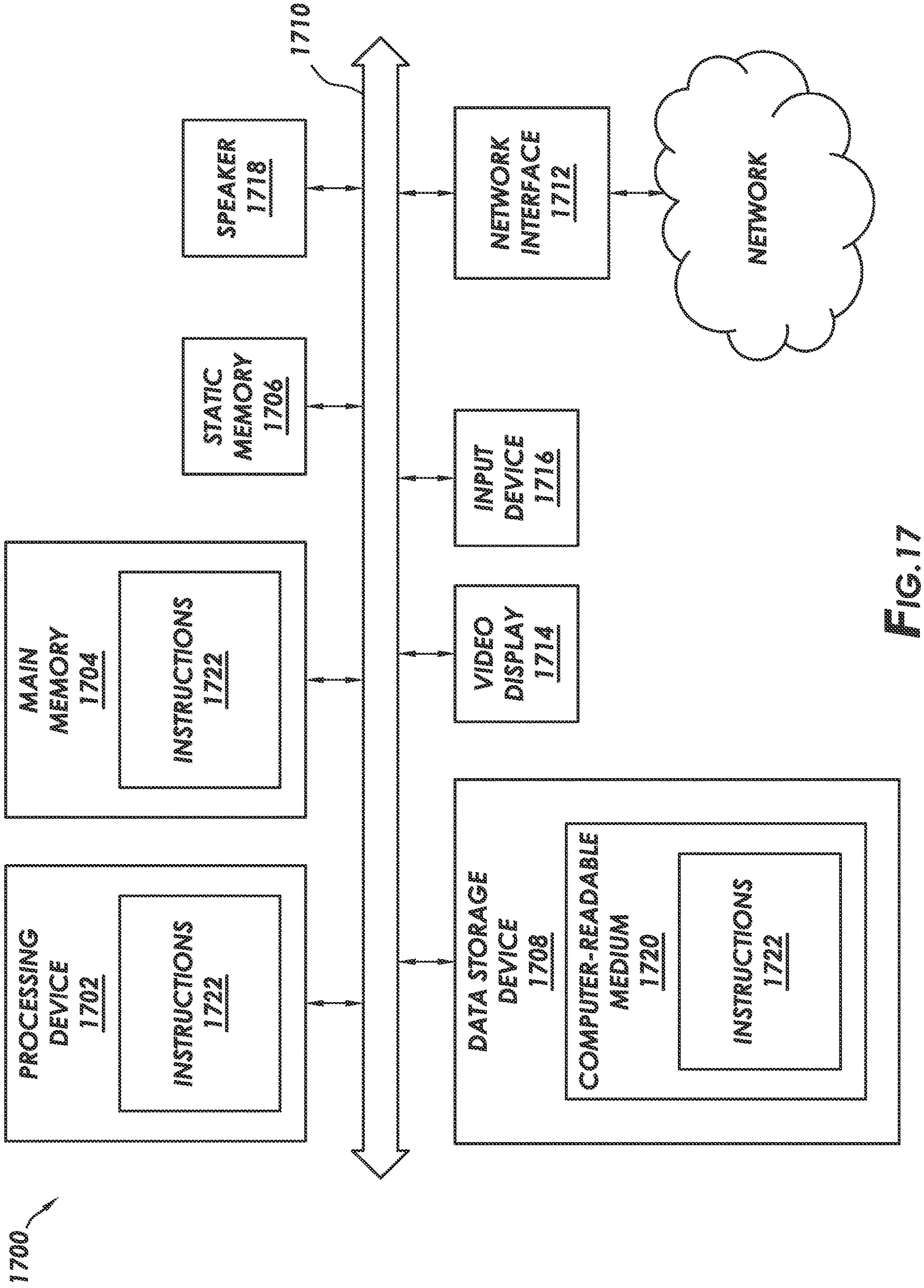
FIG. 17 shows a computer system in accordance with at least some embodiments.

FIG. 17 shows an example computer system 1700. In one example, computer system 1700 may correspond to the surgical controller 118, a tablet device within the surgical room, or any other system that implements any or all the various methods discussed in this specification. The computer system 1700 may be connected (e.g., networked) to other computer systems in a local-area network (LAN), an intranet, and/or an extranet (e.g., device cart 102 network), or at certain times the Internet (e.g., when not in use in a surgical procedure). The computer system 1700 may be a server, a personal computer (PC), a tablet computer or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1700 includes a processing device 1702, a main memory 1704 (e.g., read-only memory (ROM), flash memory, dynamic random access memory (DRAM) such as synchronous DRAM (SDRAM)), a static memory 1706 (e.g., flash memory, static random access memory (SRAM)), and a data storage device 1708, which communicate with each other via a bus 1710.

Processing device 1702 represents one or more general-purpose processing devices such as a microprocessor, central processing unit, or the like. More particularly, the processing device 1702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1702 may also be one or more special-purpose processing devices such as an application specific integrated circuit (ASIC), a field programmable gate array (FPGA), a digital signal processor (DSP), network processor, or the like. The processing device 1702 is configured to execute instructions for performing any of the operations and steps discussed herein. Once programmed with specific instructions, the processing device 1702, and thus the entire computer system 1700, becomes a special-purpose device, such as the surgical controller 118.

The computer system 1700 may further include a network interface device 1712 for communicating with any suitable network (e.g., a network operated within the device cart 102). The computer system 1700 also may include a video display 1714 (e.g., display device 114), one or more input devices 1716 (e.g., a microphone, a keyboard, and/or a mouse), and one or more speakers 1718. In one example, the video display 1714 and the input device(s) 1716 may be combined into a single component or device (e.g., an LCD touch screen).

The data storage device 1708 may include a computer-readable storage medium 1720 on which the instructions 1722 embodying any one or more of the methodologies or functions described herein is stored. The instructions 1722 may also reside, completely or at least partially, within the main memory 1704 and/or within the processing device 1702 during execution thereof by the computer system 1700. As such, the main memory 1704 and the processing device 1702 also constitute computer-readable media. In certain cases, the instructions 1722 may further be transmitted or received over a network via the network interface device 1712.

While the computer-readable storage medium 1720 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method comprising:

retaining a bone marker on a distal end of an installation tool, the bone marker comprising a polyhedron having a fiducial pattern on each of at least three outward facing surfaces of the polyhedron, an externally-threaded screw extending distally from the polyhedron, and a flange proximate to an intersection of the polyhedron and the externally-threaded screw;

positioning a distal end of the externally-threaded screw against a bone at a marker location;

screwing the externally-threaded screw into the bone by way of the installation tool; and trapping tissue against the bone beneath the flange.

2. The method of claim 1 wherein trapping tissue against the bone further comprises trapping tissue between an exterior surface of the bone and a bottom face of the flange being a polymeric material.

3. The method of claim 1 wherein trapping tissue against the bone further comprises trapping tissue between an exterior surface of the bone and a bottom face of the flange being a metallic material.

4. The method of claim 1 wherein trapping the tissue against the bone further comprises trapping the tissue with the flange, and a vector normal to a plane defined by a portion of flange beneath the polyhedron forms an acute angle with a longitudinal central axis of the externally-threaded screw.

5. The method of claim 1 wherein trapping tissue against the bone further comprises trapping tissue between an exterior surface of the bone and a bottom face of the flange defining at least one outside shape consisting of: circular; and oblong.

6. The method of claim 1 wherein retaining the bone marker further comprises:

telescoping the polyhedron into an internal volume at the distal end of the installation tool, the bone marker comprising a retention bore having an entrance aperture through an upper face of the polyhedron; and placing a retention fastener within the retention bore, the retention fastener retains the bone marker in a mating relationship with the installation tool.

7. The method of claim 6 further comprising, after screwing the externally-threaded screw into the bone, removing the retention fastener from within the retention bore.

8. The method of claim 6 wherein screwing the externally-threaded screw into the bone further comprises applying force to the flange to the exclusion of the polyhedron.

9. The method of claim 6 wherein placing the retention fastener within the retention bore further comprises threading external threads of the retention fastener into mating relationship with internal threads of the retention bore.

10. The method of claim 9 further comprising, after screwing the externally-threaded screw into the bone, unscrewing the external threads of the retention fastener from the internal threads of the retention bore.

11. The method of claim 6 wherein screwing the externally-threaded screw into the bone further comprises applying force to the at least three outward facing surfaces of the polyhedron.

12. The method of claim 11 wherein applying force to the at least three outward facing surfaces of the polyhedron further comprises applying force at a location on each of the at least three outward facing surfaces that does not overlap the respective fiducial pattern on each of the at least three outward facing surfaces.

13. A bone marker comprising:

a polyhedron defining a first outward-facing surface, a second outward-facing surface, and a third outward-facing surface;

an externally-threaded screw projecting from a side of the polyhedron, the externally-threaded screw and polyhedron are monolithic;

a retention bore having an entrance aperture through the polyhedron, the retention bore defining a retention feature on an inside surface of the retention bore;

a first fiducial pattern on the first outward-facing surface, a second fiducial pattern on the second outward-facing surface, and a third fiducial pattern on the third outward-facing surface, the first, second, and third fiducial patterns distinct from each other; and a flange disposed proximate to an intersection of the polyhedron and the externally-threaded screw.

14. The bone marker of claim 13 wherein the polyhedron is a cube.

15. The bone marker of claim 13 wherein the externally-threaded screw is a self-tapping screw.

16. The bone marker of claim 13 wherein the first, second, and third fiducial patterns are each three dimensional patterns.

17. The bone marker of claim 13 wherein the retention feature further comprises threads defined on an inside surface of the retention bore.

18. The bone marker of claim 17 wherein the externally-threaded screw comprises right-handed threads, and the threads on the inside surface of the retention bore comprises left-handed threads.

19. The bone marker of claim 13 wherein the flange further comprises a polymeric material defining a top surface, a bottom surface opposite the top surface, a throughbore defining a throughbore axis, and a thickness measured parallel to throughbore axis, the throughbore telescoped over the externally-threaded screw, and the flange disposed at the intersection of a bottom face of the polyhedron and the proximal end of the externally-threaded screw.

20. The bone marker of claim 19 wherein the flange comprises at least one material selected from a group consisting of: polymeric material; metallic material; and silicone.

21. The bone marker of claim 19 wherein the flange further comprises at least one shape selected from a group consisting of: circular; and oblong.

22. The bone marker of claim 19 further comprising:

an annular trough disposed at the intersection of the polyhedron and a proximal end of the externally-threaded screw, the annular trough circumscribing a longitudinal central axis of the externally-threaded screw; and an inside diameter of the throughbore of the flange forming a friction fit with the annular trough.

23. The bone marker of claim 19 further comprising:

an annular trough disposed at the intersection of the polyhedron and a proximal end of the externally-threaded screw, the annular trough circumscribing a longitudinal central axis of the externally-threaded screw;

an installation thread defined between threads of the externally-threaded screw and the annular trough; and an inside diameter of the throughbore disposed within the annular trough.

24. The bone marker of claim 13 wherein the flange further comprises:

an upper surface that intersects the first, second, and third outward-facing surfaces;

a lower surface that intersects the externally-threaded screw;

a diameter greater than a largest dimension of the polyhedron measured perpendicular to a longitudinal central axis of the externally-threaded screw; and the flange, the polyhedron, and the externally-threaded screw are monolithic.

25. The bone marker of claim 24 further comprising an interface feature defined by the flange, the interface feature being at least one selected from a group consisting of: an outside surface of the flange; an indention on the upper surface of the flange.

* * * * *